United States Patent [19]

Osono et al.

[11] Patent Number: 4,656,262
[45] Date of Patent: Apr. 7, 1987

[54] 7-METHOXY CEPHALOSPORIN DERIVATIVE

[75] Inventors: Takashi Osono, Tokyo; Yoshihiko Oka; Shunichi Watanabe, both of Saitama; Takeshi Saito, Tokyo; Hiroshi Gushima; Keisuke Murakami, both of Saitama; Isao Takahashi, Tokyo; Hiroshi Yamaguchi, Saitama; Toshio Sasaki, Tokyo; Kiyoshi Susaki; Shuichi Takamura, both of Saitama; Toshiaki Miyoshi, Tokyo, all of Japan

[73] Assignee: Yamanouchi Pharmaceutical Co., Ltd., Tokyo, Japan

[21] Appl. No.: 808,680

[22] Filed: Dec. 13, 1985

Related U.S. Application Data

[60] Continuation of Ser. No. 660,254, Oct. 12, 1984, abandoned, which is a continuation of Ser. No. 359,765, Mar. 19, 1982, abandoned, which is a division of Ser. No. 160,193, Jun. 17, 1980, abandoned, which is a continuation of Ser. No. 940,370, Sep. 7, 1978, abandoned, which is a continuation of Ser. No. 754,007, Dec. 27, 1976, abandoned.

[30] Foreign Application Priority Data

Dec. 25, 1975 [JP] Japan ............................ 50-155646
Jul. 26, 1976 [JP] Japan ............................ 51-88770

[51] Int. Cl.⁴ .................. C07D 501/28; A61K 31/545
[52] U.S. Cl. .................................................. 540/221
[58] Field of Search ........................ 544/21; 514/201; 540/221

[56] References Cited

U.S. PATENT DOCUMENTS 3,984,403 10/1976 Fujisawa et al. ............... 260/243 C
4,042,472 8/1977 Hall ..................................... 544/21
4,242,509 12/1980 Lunn ................................... 544/21

Primary Examiner—Nicholas S. Rizzo
Attorney, Agent, or Firm—Burgess, Ryan & Wayne

[57] ABSTRACT

The 7-methoxy-3-heterocyclic thiomethyl cephalosporin derivative possessing excellent antimicrobial activity represented by the general formula

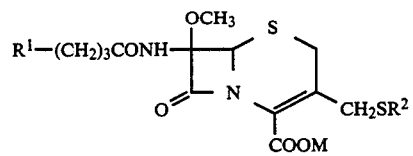

wherein $R^1$ represents

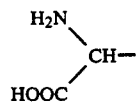

group or HOOC— group, $R^2$ represents a nitrogen-containing heterocyclic group, and M represents a hydrogen atom or a cation residue forming a salt.

1 Claim, No Drawings

7-METHOXY CEPHALOSPORIN DERIVATIVE

This application is a continuation of Ser. No. 660,254, filed Oct. 12, 1984 now abandoned, which is a continuation of Ser. No. 359,765 filed Mar. 9, 1982, now abandoned, which is a division of Ser. No. 160,193 filed June 17, 1980, now abandoned, which is a continuation of Ser. No. 940,370 filed Sept. 7, 1978, now abandoned which is a continuation of Ser. No. 754,007 filed Dec. 27, 1976, now abandoned.

DETAILED DESCRIPTION OF THE INVENTION

The present invention relates to cephalosporins having a methoxy group at the 7-position and also to a process of producing the cephalosporins. More particularly, the invention relates to cephalosporins each having a methoxy group and a 5-amino-5-carboxyvaleramide group or a 4-carboxybutyramide group at the 7-position and a heterocyclic thiomethyl group at the 3-position and also to a process of producing the cephalosporins by fermentation.

The aimed compound of this invention is shown by following general formula (A)

$$R^1-(CH_2)_3CONH-\overset{OCH_3}{\underset{O}{\overset{|}{\diagup}}}\overset{S}{\underset{N}{\diagdown}}\overset{}{\underset{COOM}{\diagdown}}CH_2-S-R^2 \quad (A)$$

wherein $R^1$ represents $$\underset{HOOC}{\overset{H_2N}{\diagdown}}CH-$$

group or HOOC— group, $R^2$ represents a nitrogen-containing heterocyclic group, and M represents a hydrogen atom or a cation residue forming a salt.

As the nitrogen-containing heterocyclic group shown by $R^2$ of the above general formula, there are illustrated a 5-carboxymethylthio-1,3,4-thiadiazol-2-yl group, a 1-methyl-1H-tetrazol-5-yl group, a 5-methyl-1,3,4-thiadiazol-2-yl group, a 1,3,4-thiadiazol-2-yl group, etc.

The cation residue shown by M for forming the salt of the cephalosporin means an inorganic residue or an organic residue. Examples of the inorganic residue are an alkali metal such as sodium, potassium, etc.; an alkaline earth metal such as calcium, magnesium, barium, etc.; and a heavy metal such as iron, copper, zinc, etc., and examples of the organic residue are bases forming quaternary salts, amine salts, etc., for example, triethylamine, diethanolamine, piperidine, morpholine, etc.

Now, the practical examples of the compounds of this invention are;

7-(5-amino-5-carboxyvaleramido)-3-(5-carboxymethylthio-1,3,4-thiadiazol-2-yl)thiomethyl-7-methoxy-$\Delta^3$-cephem-4-carboxylic acid, 7-(5-amino-5-carboxyvaleramido)-3-(1-methyl-1H-tetrazol-5-yl)thiomethyl-7-methoxy-$\Delta^3$-cephem-4-carboxylic acid, 7-(5-amino-5-carboxyvaleramido)-7-methoxy-3-(5-methyl-1,3,4-thiadiazol-2-yl)thiomethyl-$\Delta^3$-cephem-4-carboxylic acid, 7-(5-amino-5-carboxyvaleramido)-7-methoxy-3-(1,3,4-thiadiazol-2-yl)thiomethyl-$\Delta^3$-cephem-4-carboxylic acid, 7-(4-carboxybutyramido)-3-(5-carboxymethylthio-1,3,4-thiadiazol-2-yl)thiomethyl-7-methoxy-$\Delta^3$-cephem-4-carboxylic acid, 7-(4-carboxybutyramido)-3-(1-methyl-1H-tetrazol-5-yl)-thiomethyl-7-methoxy-$\Delta^3$-cephem-4-carboxylic acid, 7-(4-carboxybutyramido)-7-methoxy-3-(5-methyl-1,3,4-thiadiazol-2-yl)thiomethyl-$\Delta^3$-cephem-4-carboxylic acid, 7-(4-carboxybutyramido)-7-methoxy-3-(1,3,4-thiadiazol-2-yl)thiomethyl-$\Delta^3$-cephem-4-carboxylic acid, and the salts of these compounds.

Some 7-methoxy-3-heterocyclethio methyl cephalosporins are described to be obtained by chemical syntheses in British Pat. No. 1,321,412 (1970) but no practical physical and chemical properties of these compounds are disclosed in the British patent.

The object of this invention is to provide novel 7-methoxy cephalosporin derivatives and further to provide a process of producing these derivatives by fermentation.

Cephalosporins show excellent antimicrobial activities to gram positive and negative bacteria and among these compounds, the cephalosporin derivatives having a methoxy group at the 7-position and a heterocyclic thiomethyl group at the 3-position show particularly excellent effect for the treatment of serious diseases caused by the infection with the bacteria such as Pseudomonas and Proteus species, to which ordinary antibiotics are ineffective, or with the bacteria non-sensitive to ordinary cephalosporins having no methoxy group at the 7-position. These compounds are usually produced by first preparing the corresponding compounds having an acetoxymethyl group or a carbamoyloxymethyl group at the 3-position by a fermentation method and then reacting the products with a heterocyclic thiol compound.

On the other hand, the present invention has such a merit that the compound having a heterocyclic thiomethyl group at the 3-position can be obtained directly by a single fermentation step. The compound thus obtained is the compound of general formula (A) wherein $R^1$ is $$\underset{HOOC}{\overset{H_2N}{\diagdown}}CH-$$

group (hereinafter, referred to as Aa). The compounds of formula A ($R^1$=Aa) show excellent antimicrobial activities themselves and further the antimicrobial activities and the antimicrobial spectra of the compounds can be increased or changed by replacing the acyl group side chain of the 7-position shown by

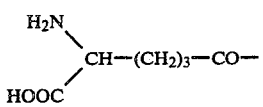

with other acyl groups such as, for example, α-aminophenylacetyl group, α-carboxyphenylacetyl group, α-sulfophenylacetyl group, α-hydroxyphenylacetyl group, pyridylthioacetyl group, thiadiazolylthioacetyl group, triazolylacetyl group, cyanomethylthioacetyl group, trifluoromethylthioacetyl group, etc., thus the compounds of formula A ($R^1$=Aa) are also useful as the intermediate compounds for producing these derivatives having these acyl groups. For example 7β-cyanomethylthioacetamido-7α-methoxy-3-(1-methyltetrazol-5-ylthiomethyl)-$\Delta^3$-cephem-4-carboxylic acid and 7α-methoxy-3-(1-methyltetrazol-5-ylthiomethyl)-7β-(trifluoromethylthioacetamido)-$\Delta^3$-cephem-4-carboxylic acid.

The compounds of formula A ($R^1$=Aa) show a property as an amphoteric material since the compounds have one amino group and two carboxy groups in the molecule and hence the isolation and purification of the compound produced is troublesome. However, when group $R^1$ of the compounds is converted from Aa to HOOC— group (hereinafter, referred to as Ab), the compounds of formula A ($R^1$=Ab) merely show the acidic property, which facilitates the isolation and purification of the compound, as well as the compound become soluble in organic solvents, which makes it profitable to perform the subsequent reaction. Therefore, the compounds are also useful as the intermediate compounds for producing the derivatives having the aforesaid acyl groups.

An example of the microorganisms useful for producing the 7-methoxycephalosporin antibiotics belonging to the Streptomyces used this invention is a new strain, which is *Streptomyces oganonensis* Y-G19Z strain previously isolated by the inventors from the soil at Ogano-Town, Chichibugun, Saitama Prefecture, Japan. This strain has been deposited in the Institute of Microbial Industry, Agency of Industrial Science and Technology, Ministry of International Trade and Industry, Japan, under an accession No. FERM-P 2725 and also in American Type Culture Collection, 12301 Parklawn Drive, Rockville Md. 20852, USA under ATCC No. 31167. The mycological properties of the strain are as follows:

I. Morphological characteristics of *S. organonensis* Y-G19Z strain:

It grows both on natural and synthetic media with formation of well branched substrate mycelium, while formation of aerial mycelium is not sufficient and hence the formation of spores is poor. Spore chains are straight, belong to R (Rectus) or RF (Rectiflexibiles) type and bear 10–50 spores on each chain. Spores are elliptical, spherical or cylindrical in shape and 0.45–0.60×0.55–0.90μ in size. Spore surface is smooth. Neither flagellate spore nor sporangium was observed.

II. Cultural Charactristics of *S. oganonemsis* Y-G19Z strain:

| Medium | Growth | Aerial mycelium | Soluble pigment |
| --- | --- | --- | --- |
| Czapek's agar | very poor, white | scant white | none |
| Glucose Czapek's agar | good, cream yellow | fair, yellowish gray | none very slightly |
| Glucose asparagine agar | good, white | poor, white | none |
| Glycerol asparagine agar | good, white to yellowish white | poor white to yellowish white | none |
| Inorganic salt starch agar | good, yellowish gray to pale yellowish brown | poor, yellowish gray | none |
| Tyrosine agar | good, pale yellow | poor, yellowish gray | slightly, pale yellowish gray |
| Iron and yeast extract tyrosine agar | good, pale yellow to yellowish brown | good, brownish white to yellowish gray | very slightly light brownish gray |
| Nutrient agar | good, pale yellowish brown | good, powdery pale orange to pale brown | slightly, yellowish brown |
| Bennett's agar | good, pale yellowish brown | good, brownish gray, pale orange to pale pink | very slightly |
| Calcium malate agar | moderate cream | none | none |
| Potato plug | good, pale yellowish brown | good, yellowish gray to pale brownish gray | brownish gray to dark yellowish brown |
| Blood agar | good, olive gray to dark olive gray | none | yellowish gray to dark reddish brown |
| Loeffler's serum meidum | good | none | none |

III. Physiological properties of *S. oganonensis* Y-G19Z strain:

| | |
| --- | --- |
| Tyrosinase formation | negative |
| Nitrate reduction | positive |

-continued

| | |
|---|---|
| Skim milk coagulation | positive, weakly |
| Skim milk peptonization | positive, weakly |
| Hydrolysis of starch | positive |
| Liquefaction of gelatin | positive, weakly |
| Cellulose decomposition | negative |
| Hemolysis | positive |
| Solubilization of calcium malate | positive |

Utilization of carbon compounds by S. oganonensis Y-G19Z

| Carbon source | Utilization |
|---|---|
| Glucose | + |
| Arabinose | + |
| Sucrose | − |
| Xylose | + |
| Inositol | − |
| Mannitol | + |
| Fructose | + |
| Rhamnose | − |
| Rhaffinose | − |

Characteristic features of Streptomyces oganonensis Y-G19Z strain: are summarized as follows:
1. It belongs to non-chromogenic Streptmyces strain.
2. Its aerial mycelium is straight without verticils (R or RF type).
3. Spores are spherical or elliptical.
4. Spore surface is smooth.
5. It gives pale yellowish gray to pale yellowish brown growth on various media.
6. Color of aerial mycelium is brownish white, yellowish white and yellowish gray.
7. Antibiotic substance Y-G19ZD3 belonging to 7-methoxy cephalosporin group is produced.

On searching known strains having the above properties, the following species may be mentioned as the most closely related strains. Streptomyces globisporus, described in S. A. Waksman: the Actinomycetes 2, 218 (1961) and International Journal of Systematic Bacteriology, 18, (4) 324–325 (1968).

However, when compared with S. globisporus disclosed in the above literatures, strain Y-G19Z differs from it in the following points shown in the table.

TABLE

| Characteristic | Y-G19Z | S. globisporus |
|---|---|---|
| Size of spore (μ) | 0.45–0.60 × 0.55–0.90 | 1.2–1.4 × 1.8–2.0 or 0.9–1.4 spherical |
| Soluble pigment on glycerol asparagine medium | none | yellow to greenish yellow |
| Rhamnose utilization | negative | positive |
| Starch hydrolysis | strong | weak |
| Skim milk coagulation | positive | negative |
| Skim milk peptonization | weak | strong |
| Production of cephalosporin antibiotics | positive | negative |

As is clear from the differences shown in the above table, the strain used in this invention is a new strain different from the aforesaid known strains.

Since Y-G19Z strain has been confirmed to be a new strain from the above observation results, it is designated "Streptomyces oganonensis".

We explained above about the Streptomyces oganonensis Y-G19Z strain as a 7-methoxy cephalosporin antibiotic producing strain but as the strains belonging similarly to the genus Streptomyces, the following strains are known to produce 7-methoxy cephalosporin antibiotics. That is, they are Streptomyces griseus, Streptomyces viridochromogenes, Stroptomyces fimbriatus, Streptomyces halstedii, Streptomyces rochei, Streptomyces cinnamonensis, Streptomyces chartreusis, and Streptomyces lactamdurans (see Japanese Patent Application Laid Open No. 3286/'71 and Belgian Pat. No. 764,160), and Streptomyces lipmanii (see U.S. Pat. No. 3,719,563), Streptomyces clavuligerus (see Japanese Patent Publication No. 45,594/'74), Streptomyces wadayamensis (see Japanese Patent Application Laid Open No. 26488/'74), Streptomyces jumonjinensis (see Japanese Patent Application Laid Open No. 42893/'74), Streptomyces heteromorphus and Streptomyces panayensis (see Japanese Patent Application Laid Open No. 53594/'75), and Streptomyces chartreusis SF-1623 (see Japanese Patent Application Laid Open Nos. 82291/'75 and 121,488/'75).

However, the strains used in this invention are not limited to the aforesaid strains, any strains which belong to the genus Streptomyces and can produce 7-methoxy cephalosporin antibiotics may be used in this invention.

Now, the production of the aimed compound A ($R^1=Aa$) is carried out by cultivating the aforesaid 7-methoxy cepharosporin antibiotics producing strain in an ordinary culture medium having added thereto a heterocyclic thiol corresponding to the heterocyclic thio group to be introduced to the 3-position as aimed at.

Examples of the heterocyclic thiols added to the culture medium in this invention are, for example, pyrrolethiol, imidazolethiol, dihydroimidazolethiol, pyrazolethiol, triazolethiol, tetrazolethiol, methyltetrazolethiol, pyridinethiol, diazinethiol, thiophenethiol, thiazolethiol, dihydrothiazolethiol, thiadiazolethiol, thiatriazolethiol, furanthiol, pyranthiol, oxazolethiol, isoxazolethiol, oxadiazolethiol, indolethiol, benzimidazolethiol, benzoxazolethiol, benzothiazolethiol, triazolopyridinethiol, thianthrenethiol, purinethiol, etc. These heterocyclic rings may have one or more substituents such as a halogen atom, amino group, nitro group, alkyl group, hydroxy group, alkoxy group, aryl group, aralkyl group, furyl group, thienyl group, oxazolyl group, carboxy group, carboxymethyl group, carboxyalkylthio group, carboxyalkyloxy group, etc.

These heterocyclic thiols may be used as the salts thereof and these salts are inorganic salts such as alkali metal salts, alkaline earth metal salts, ammonium salts, etc., and the salts with organic bases such as triethylamine, triethanolamine, dicyclohexylamine, lysine, arginine, histidine, a basic water-soluble antibiotic, e.g., kanamycin, alkaloid, basic protein, etc. The salts having a high water solubility may be selectively used, if necessary and further when the heterocyclic thiols show a strong toxicity to the antibiotics producing strains, the salts sparingly soluble in water can be selectively used.

Moreover, as compounds which can be converted into the aforesaid heterocyclic thiol during cultivation, there is illustrated compounds which connect to an organic or inorganic SH compound by S—S bond. Such S—S compounds form the aforesaid heterocyclic thiol in a culture medium or in the mycelium in the culture medium by a chemical conversion or/and the enzymatic activity of the mycelium or further the compound sometime may be utilized as it is as the precursor. Examples of these S—S compounds are as follows;

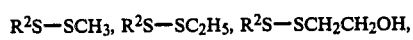

$R^2S-SCH_3$, $R^2S-SC_2H_5$, $R^2S-SCH_2CH_2OH$,

R²S—SCH₂CHCOOH, R²S—SG (wherein G represents a
       |
       NH₂ glutathione residue and/hereinafter having same meaning),

R²S—SCH₂CH₂NH₂, R²S—SCoA (wherein CoA represents coenzyme A residue), R²S—SCHCONHCH₂COOH,
                          |
                          CH₃

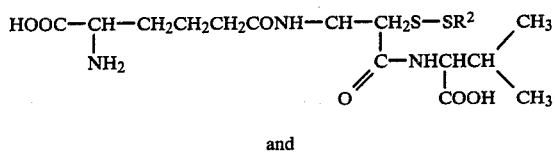

and

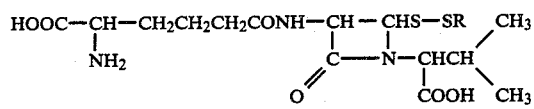

Also, two molecules of a same heterocyclic thiol bonded by the S—S bond can be used as R²S—SR².

Furthermore, when the antibiotics producing strain has a sulfuric acid reducing faculty, R²—SO₃H, R²—SO₂H, R²—SOH, or the salts thereof may be used in place of R²SH.

The production of the aimed antibiotics of this invention is performed by cultivating the 7-methoxy cephalosporin antibiotics producing strains belonging to the genus Streptomyces in a culture medium with the addition of the above-described heterocyclic thiol or the salt or derivative thereof. The cultivation is carried out according to conventional method for general microorganisms but submerged cultivation in a liquid culture medium is usually preferred. Any culture media containing nutrients for the 7-methoxy cephalosporin antibiotics producing strains belonging to the genus Streptomyces can be employed. That is, synthetic culture media, semi-synthetic culture media, and natural culture media containing the aforesaid nutrients can be used in this invention. For the composition of the culture medium, glucose, sucrose, mannitol, glycerol, dextrin, starch, vegetable oil, etc., can be used as the carbon sources and meat extract, peptone, gluten meal, cotton seed meal, soybean meal, peanut meal, fish meal, corn steep liquor, dry yeast, yeast extract, ammonium sulfate, ammonium nitrate, urea, and other organic and inorganic nitrogen sources can be used as the nitrogen sources. Also, if necessary, a metal salt such as the sulfates, nitrates, chlorides, carbonates, phosphates, etc., of Na, K, Mg, Ca, Zn, and Fe may be added to the culture medium. Still further, if necessary, materials for promoting the formation of antibiotics or defoaming agent such as methionine, cystein, cystine, methyl oleate, lard oil, silicone oil, surface active agents, etc. may be suitably added to the culture medium.

The aforesaid heterocyclic thiol or the salt or the derivative thereof is usually added at a concentration of 0.1–5 mg./ml., preferably 0.5–2 mg./ml. as the heterocyclic thiol and it may be added to the culture medium at one fell swoop before cultivation or added thereto in several divided parts at the initial stages of the cultivation.

It is generally desirable to carry out the cultivation under an aerobic condition and further the cultivation temperature is usually from about 18° C. to about 35° C., preferably about 30° C. Moreover, desirable results are obtained when the pH of the culture medium is maintained at about 5–10, preferably about 6–8. The cultivation period of time depends upon the composition and the temperature of the culture medium employed but is generally from about 3 days to about 10 days and thus the aimed material is selectively accumulated in the medium after the cultivation is finished.

The aimed material of this invention can be isolated or recovered from the cultivated broth by an ordinary manner employed for isolating antibiotics from the cultivated broth of mycelium. The aimed antibiotic of this invention is mainly contained in the culture broth and hence after removing mycelium therefrom by centrifugal separation or filtration, the effective aimed material is extracted from the filtrate. That is, the aimed material is separated, recovered, and purified from the filtrate by means generally used for producing antibiotics, such as those utilizing the differences in solubility in a suitable solvent the differences in adsorptive affinity to various adsorbents, or the differences in partition between two liquid phases. These methods may be, if necessary, used individually or as a proper combination of them, or further may be repeatedly used.

Several practical examples of the novel 7-methoxy cephalosporin compounds of this invention are shown below:

I. 7-(5-Amino-5-carboxyvaleramido)-3-(5-carboxymethylthio-1,3,4-thiadiazol-2-yl)thiomethyl-7-methoxy-Δ³-cephem-4-carboxylic acid;

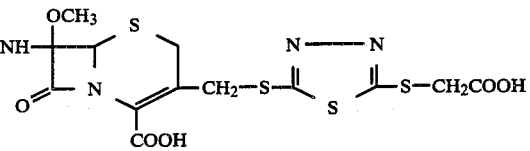

Addition compound: 5-mercapto-1,3,4-thiadiazol-2-thioacetic acid;

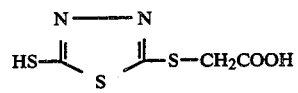

The physical and chemical properties of the aimed compound I of general formula A (R¹=Aa,

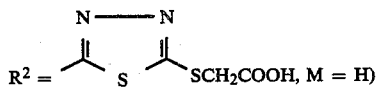

R² = , M = H)

are as follows:
(1) white powder.
(2) Begins to melt from 156°–160° C. and to become brown and decompose from about 170° C.

(3) Easily soluble in water, sparingly soluble in methanol, and scarcely soluble in other organic solvents.

(4) Amphoteric material showing ninhydrin reaction positive.

(5) Gives the ultraviolet absorption spectra as shown in FIG. 1 of the accompanying drawings when measured in a 1/100M phosphate buffer solution having a pH of 6.4 and shows the absorption maximum at 287 mµ.

(6) Gives the infrared absorption spectra as shown in FIG. 2 when measured as potassium bromide tablet and shows absorptions at 3413 cm$^{-1}$, 2920 cm$^{-1}$, 1763 cm$^{-1}$, 1620 cm$^{-1}$, 1515 cm$^{-1}$, and 1380 cm.$^{-1}$ (7) Gives the following signals in the nuclear magentic resonance spectrum when measured using TMS as an external standard in heavy water;

δ value (p p m): 2.35 (4H, multiplet), 2.96 (2H, multiplet), 4.00 (3H, singlet), 3.73–4.33 (2H, quartet, J=18 Hz), 4.25 (1H, multiplet), 4.44 (2H, singlet), 4.42–4.91 (2H, quartet, J=14 Hz), 5.63 (1H, singlet).

(8) The aimed material obtained as the purest state at present shows the following elemental-analytical value: C: 35.95%, H: 3.87%, N: 10.85%, S: 18.33%.

(9) Gives α-aminoadipic acid when hydrolyzed by 6N hydrochloric acid.

(10) The mass spectrum of this compound after N-chloroacetylating the compound and converting the product into the methyl ester gives the following fragment of m/e 392, i.e.,

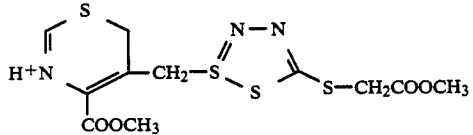

Considering the results shown above, it is clear that this compound is a 7-methoxycephalosporin compound since the compound gives an absorption at 1763 cm$^{-1}$ (cyclic lactam) in the infrared absorption spectra and the presence of the signals at 4.00 p p m (3H, singlet, 7-OCH$_3$), 5.63 p p m (1H, singlet, 6-CH), 3.73–4.33 (2H, quartet, J=18 Hz, 2-CH$_2$), and 4.42–4.91 (2H, quartet, J=14 Hz, 3-side chain CH$_2$) in the nuclear magnetic resonance spectra, the compound gives α-aminoadipic acid on acid hydrolysis, and further from the facts that the compound gives the absorption at 4.44 p p m (2H, singlet, CH$_2$ of —S—CH$_2$—COOH) in the nuclear magnetic resonance spectra and gives the fragment of m/e 392 in the mass spectra of the derivative, the compound has been decided to have the aforesaid structure having introduced thereto the heterocyclic thiol.

II. 7-(5-Amino-5-carboxyvaleramido)-3-(1-methyl-1H-tetrazol-5-yl)thiomethyl-7-methoxy-Δ$^3$-cephem-4-carboxylic acid:

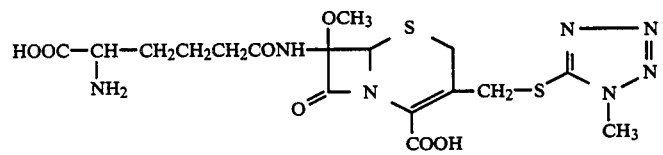

Addition compound: 5-mercapto-1-methyl-1H-tetrazole.

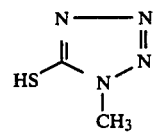

The physical and chemical properties of the aimed compound II of formula A (R$^1$=Aa,

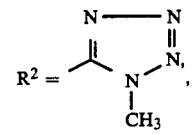

M=H) are as follows:

(1) white powder.

(2) Gives brown discoloring and decomposition at 160°–170° C.

(3) Easily soluble in water, sparingly soluble in methanol, and scarcely soluble in other organic solvents.

(4) Amphoteric material showing ninhydrin reaction positive.

(5) Gives the ultraviolet absorption spectra as shown in FIG. 3 when measured in a 1/100M phosphate buffer solution having a pH of 6.4 and has the absorption maximum at 273 mµ.

(6) Gives the infrared absorption spectra as shown in FIG. 4 when measured as potassium bromide tablet and shows the absorptions at 3413 cm$^{-1}$, 2920 cm$^{-1}$, 1765 cm$^{-1}$, 1620 cm$^{-1}$, 1515 cm$^{-1}$, and 1390 cm.$^{-1}$ (7) The nuclear magnetic resonance spectra measured using TMS as the external standard in heavy water shows the following signals:

δvalue (p p m): 2.36 (4H, multiplet), 2.96 (2H, multiplet), 3.98 (3H, singlet), 4.38 (1H, multiplet), 4.50 (3H, singlet), 5.59 (1H, singlet).

(8) The aimed material obtained at the purest state at present shows the following elemental-analytical value: C: 37.48%, H: 4.25%, N: 16.74%, and S: 10.90%.

(9) Gives α-aminoadipic acid when hydrolyzed by 6N hydrochloric acid and gives 5-mercapto-1-methyl-1H-tetrazole when hydrolyzed in methanol by Dowex 50 W (H-type, trade name).

Considering from the whole results, it is clear that the compound is a 7-methoxycephalosporin compound since the compound gives the signals at 3.98 p p m (3H, singlet, 7-OCH$_3$) and 5.59 p p m (1H, singlet, 6-CH) in the nuclear magnetic resonance spectra, the absorption at 1765 cm$^{-1}$ (cyclic lactam) in the infrared absorption spectra, and gives α-aminoadipic acid by acid hydrolysis thereof, and further from the facts that the absorption is present at 4.50 p p m (3H, singlet, tetrazole-N-methyl) in the nuclear magnetic resonance spectra and also 5-mercapto-1-methyl-1H-tetrazole is obtained by mild hydrolysis, the compound has been decided to have the aforesaid structure having introduced thereto the heterocyclic thiol.

III. 7-(5-Amino-5-carboxyvaleramido)-7-methoxy-3-(5-methyl-1,3,4-thiadiazol-2-yl)thiomethyl-Δ³-cephem-4-carboxylic acid.

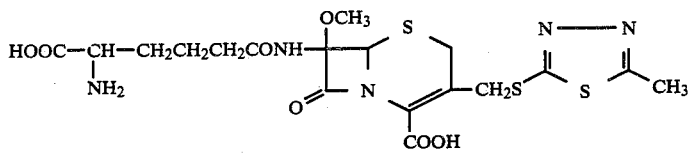

Addition compound: 2-mercapto-5-methyl-1,3,4-thiadiazole:

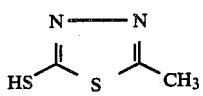

The physical and chemical properties of the aimed compound III of formula A (R¹=Aa,

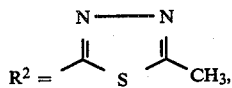

M=H) are as follows:

(1) light yellow-white powder.

(2) Shows no distinct melting point and gives brown discoloring and decomposition at about 170° C.

(3) Easily soluble in water, slightly soluble in methanol, but insoluble in other organic solvents.

(4) Amphoteric material showing ninhydrin reaction positive.

(5) Gives the ultraviolet absorption spectra as shown in FIG. 5 when measured in a 1/100M phosphate buffer solution having a pH of 6.4 and has the absorption maximum at 272 mμ.

(6) Gives the infrared absorption spectra as shown in FIG. 6 when measured as potassium bromide tablet and shows the absorptions at 3420 cm⁻¹, 2930 cm⁻¹, 1765 cm⁻¹, 1610 cm⁻¹, 1515 cm⁻¹, and 1385 cm⁻¹.

(7) The nuclear magnetic resonance spectra measured using TMS as the external standard in heavy water gives the following signals:

δ value (p p m): 2.34 (4H, multiplet), 2.95 (2H, multiplet), 3.19 (3H, singlet), 3.72–4.31 (2H, quartet, J=18 Hz), 3.99 (3H, singlet), 4.26 (1H, multiplet), 4.40–4.95 (2H, quartet, J=14 Hz), 5.63 (1H, singlet).

(8) The aimed compound obtained in the purest state at present shows the following elemental-analytical value: C: 37.82%, H: 4.01%, N: 12.90%, S: 14.97%.

(9) Gives α-aminoadipic acid when hydolyzed by 6N hydrochloric acid and also gives 2-mercapto-5-methyl-1,3,4-thiadiazole when hydrolyzed in methanol by Dowex 50 W (H type, trade name).

Considering from the whole results, it is clear that the compound is a 7-methoxycephalosporin compound since the compound gives the absorption at 1765 cm⁻¹ (cyclic lactam) in the infrared absorption spectra, the signals at 3.99 p p m (3H, singlet, 7-OCH₃), 5.63 p p m (1H, singlet, 6-CH), 3.72–4.31 p p m (2H, quartet, J=18 Hz, 2-CH₂), 4.40–4.95 (2H, quartet, J=14 Hz, 3-side chain CH₂), and gives α-aminoadipic acid by the acid hydrolysis, and further from the facts that the absorption of 3.19 p p m (3H, singlet, thiadiazole C—CH₃) is present in the nuclear magnetic resonance spectra and also 2-mercapto-5-methyl-1,3,4-thiadiazole is obtained by mild hydrolysis, the compound has been decided to have the aforesaid structure having introduced thereto the heterocyclic thiol.

IV. 7-(5-Amino-5-carboxyvaleramido)-7-methoxy-3-(1,3,4-thiadiazol-2-yl)thiomethyl-Δ³-cephem-4-carboxylic acid.

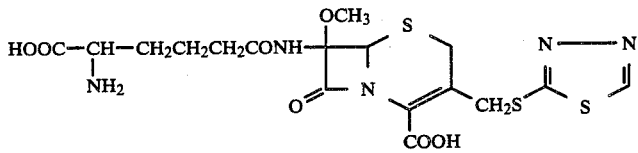

Addition compound: 2-mercapto-1,3,4-thiadiazole.

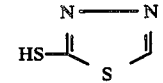

The physical and chemical properties of the aimed compound IV of formula A (R¹=Aa,

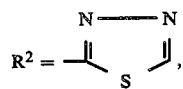

M=H) are as follows:

(1) Light yellow white powder.

(2) Shows no distinct melting point but gives brown discoloring and decomposition at about 175°–180° C.

(3) Easily soluble in water, slightly soluble in methanol, but insoluble in other organic solvents.

(4) Amphoteric material showing ninhydrin reaction positive.

(5) Gives the ultraviolet absorption spectra as shown in FIG. 7 when measured in a 1/100M phosphate buffer solution of a pH of 6.4 and has the maximum absorption at 274 mμ.

(6) Gives the infrared absorption spectra as shown in FIG. 8 when measured as potassium absorption spectra as shown in the absorptions at 3400 cm⁻¹, 2925 cm⁻¹, 1765 cm⁻¹, 1610 cm⁻¹, 1515 cm⁻¹, and 1365 cm⁻¹.

(7) The magnetic resonance spectra measured using TMS as the external standard in heavy water gives the following signals:

δ value (p p m): 2.30 (4H, multiplet), 2.93 (2H, multiplet), 3.69–4.29 (2H, quartet, J=18 Hz), 3.97 (3H, singlet), 4.26 (1H, multiplet), 4.45–4.99 (2H, quartet, J=14 Hz), 5.56 (1H, singlet), 9.85 (1H, singlet).

(8) The aimed material obtained in the purest state at present shows the following elemental-analytical value: C: 37.53%, H: 4.36%, N: 12.77%, S: 16.42%.

(9) Gives α-aminoadipic acid when hydrolyzed by 6N hydrochloric acid and also gives 2-mercapto-1,3,4-thiadiazole when hydrolyzed in methanol by Dowex 50 W (H type, trade name).

Considering the whole results, it is clear that the compound is a 7-methoxycephalosporin compound since the compound gives the absorption at 1765 cm$^{-1}$ in the infrared absorption spectra, gives the signals at 3.97 p p m (3H, singlet, 7-OCH$_3$), 5.56 p p m (1H, singlet, 6-CH), 3.69–4.29 p p m (2H, quartet, J=18 Hz, 2-CH$_2$), 4.45–4.99 (2H, quartet, J=14 Hz, 3-side chain CH$_2$), and also gives α-aminoadipic acid by acid hydrolysis and further from the facts that the absorption of 9.85 p p m (1H, singlet, thiazole CH) is present in the nuclear magnetic resonance spectra and further 2-mercapto-1,3,4-thiadiazole is obtained by mild hydrolysis, the compound of this invention has been decided to have the aforesaid structure having introduced thereto the heterocyclic thiol.

Then, the results of the various chromatographic analyses and paper electrophoresis about the aimed compounds I, II, III, and IV of this invention are shown below.

The Rf values of these compounds in the thin layer chromatography using microcyrstalline cellulose (Avicel SF, trade name) are shown in the following table.

|  | 1 | 2 | 3 |
|---|---|---|---|
| Aimed compound I | 0.39 | 0.37 | 0.32 |
| Aimed compound II | 0.39 | 0.34 | 0.31 |
| Aimed compound III | 0.43 | 0.43 | 0.40 |
| Aimed compound IV | 0.39 | 0.38 | 0.33 |
| Cephalosporin C | 0.37 | 0.36 | 0.31 |
| 7-Methoxy-cephalosporin C | 0.41 | 0.36 | 0.32 |
| Cephamycin C | 0.37 | 0.36 | 0.31 |
| Y-G19Z-D3 | 0.26 | 0.26 | 0.22 |
| Y-19Z-D2 | 0.39 | 0.32 | 0.26 |

Developing solvent system (volume ratio) used:
1. Isopropanol:n-butanol:acetic acid:water (21:3:7:9).
2. n-Butanol:acetic acid:water (4:1:2).
3. n-Butanol:acetic acid:water (6:1.5:2.5).

The control sample, cephamycin C is 7-(5-amino-5-carboxyvaleramido)-3-carbamoyloxymethyl-7-methoxy-Δ$^3$-cephem-4-carboxylic acid.

Y-G19Z-D3 and Y-G19Z-D2 used in the above comparison tests are the novel 7-methoxycephalosporin compounds previously separated from the culuture liquid of the Streptomyces oganonensis by the same inventors (see, Japanese Patent Application Nos. 109,753/'74 and 146,593/'75).

Also, the Rf values obtained by paper partition chromatography using Wattman No. 1 filter paper and also a developing solvent system of n-butanol:acetic acid:water (4:1:2 by volume ratio) are as follows:

|  | Rf value |
|---|---|
| Aimed compound I | 0.40 |
| Aimed compound II | 0.39 |
| Cephalosporin C | 0.36 |
| 7-Methoxy-cephalosporin C | 0.40 |
| Cephamycin C | 0.35 |
| Y-G19Z-D3 | 0.24 |
| Y-G19Z-D2 | 0.25 |

Then, the compounds were analyzed using Hitachi 635 High Speed Liquid Chromatography Apparatus, the results being as follows:
Column: 3×500 mm stainless steel column.
Resin: Hitachi 2610 (cationic exchange resin, trade name).
Developing solvent system: 0.2M citrate buffer solution (pH 3.6).
Flow speed: 0.6 ml/min.
Chart speed: 1.0 cm./min.

|  | Retention time |
|---|---|
| Aimed compound I | 5 min. 33 sec. |
| Aimed compound II | 6 min. 00 sec. |
| Aimed compound III | 9 min. 35 sec. |
| Cephalosporin C | 5 min. 18 sec. |
| 7-Methoxy-cephalosporin C | 5 min. 09 sec. |
| Cephamycin C | 5 min. 18 sec. |
| Y-G19Z-D3 | 3 min. 42 sec. |
| Y-G19Z-D2 | 3 min. 42 sec. |

Also, the results obtained by analysis using the above apparatus under the following conditions are shown in the following table.
Column: μ Bondapak C$_{18}$ (made by Waters Ltd.) of 4×300 mm.
Developing solvent system: acetonitrile:0.1% acetic acid solution (pH 3.3) (1:9 by volume ratio)
Flow speed: 0.8 ml./min.
Chart speed: 1.0 cm./min.

|  | Retention time |
|---|---|
| Aimed compound I | 3 min. 14 sec. |
| Aimed compound II | 1 min. 52 sec. |
| Aimed compound III | 2 min. 55 sec. |
| Aimed compound IV | 1 min. 56 sec. |

The results obtained by high-voltage paper electrophoresis are as follows:
Filter paper: Wattman No. 1.
Developing solvent: 10% acetic acid (pH 2.2).
Voltage: 42 volts/cm.
Running time: 1 hour.

|  | Migration distance |
|---|---|
| Aimed compound I | −3.6 cm. |
| Aimed compound II | −3.3 cm |
| Aimed compound III | −3.6 cm |
| Aimed compound IV | −3.9 cm |
| Cephalosporin C | −3.5 cm |
| 7-Methoxy-cephalosporin C | −3.4 cm |
| Cephamycin C | −3.5 cm |
| Y-G19Z-D3 | −6.1 cm |
| Y-G19Z-D2 | −6.1 cm |
| Cysteic acid | −7.5 cm |
| Glutathione | −1.2 cm |

Then, the antibacterial activity of the aimed compounds I, II, III, and IV of this invention is shown in the following table together with that of cephalosporin C as comparison. Heart infusion agar disc method (500 γ/ml. solution used).

The numeral values in the table show the diameter (mm.) of the inhibition zone.

|  | I | II | III | IV | C |
|---|---|---|---|---|---|
| *Sarcina lutea* ATCC 9341 | 0 | 0 | 0 | 0 | 14.0 |
| *Staphylococcus aureus* 209 P | 0 | 0 | 0 | 0 | 12.8 |
| *Bacillus subtiris* ATCC 6633 | 0 | 0 | 0 | 0 | 23.1 |
| *Escherichia coli* NIHJ | 19.2 | 18.7 | 14.2 | 13.0 | 10.4 |
| *Klebsiella pneumoniae* | 21.8 | 23.5 | 23.0 | 23.0 | 13.0 |
| *Salmonella gallinarum* | 24.0 | 25.2 | 23.5 | 25.1 | 23.5 |
| *Proteus vulgaris* OX 19 | 22.6 | 20.2 | 20.0 | 21.0 | 17.5 |
| *Proteus mirabilis* IMF OM-9 | 22.2 | 19.8 | 19.5 | 23.0 | 23.0 |

(Note):
I: Compound I of this invention.
II: Compound II of this invention.
III: Compound III of this invention.
IV: Compound IV of this invention.
C: Cephalosporin C (comparison)

Now, each of the compounds I, II, III, and IV of this invention can be administered in various forms singly or in combination with other medicaments. That is, the compounds of this invention can be administered orally, by intramuscular injection, by intravenous injection, etc., in the forms of capsules, tablets, powders, granules, solutions, and suspensions. Various carriers are added for the preparations, for example, mannitol, sucrose, glucose, sterilized distilled water, saline solution, and a vegetable oil such as peanut oil, sesame oil. Furthermore, other ingredients such as a stabilizer, a binding agent, an antioxidant, a preservative, a lubricant used at preparing tablets, a suspending agent, a viscosity agent, a perfume, etc., may be added.

As the salts of the compounds of formula A ($R^1$=Aa), the salts of inorganic or organic bases which are pharmacologically nontoxic or useful are used. The doses of the medicaments mainly depend upon the condition and the weight of the host and also depend on the administration manner, i.e. oral administration or parenteral administration. In general, 50 mg./kg. is administered once or in a few times per day.

The compounds A ($R^1$=Aa) of this invention show excellent antimicrobial activities and are used for the prophylaxis and treatment of diseases of men and animals as well as are suitably used as the intermediates for prducing other effective 7-methoxycephalosporin derivatives. In any case, it is preferred that the compound of formula A ($R^1$=Aa) be isolated as the pure produce or as a highly concentrated crude product.

In particular, when the substituted group

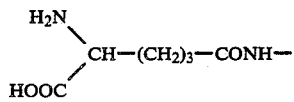

at the 7-position of the compound of formula A ($R^1$=Aa) is replaced by other acylamide group, the amphoteric property disappears and the product of acidic property thus modified becomes convenient for isolation as well as becomes soluble in organic solvents, and the subsequent reaction can be carried out without difficulty. Therefore, the modification of the compound of formula A ($R^1$=Aa) into A ($R^1$=Ab) as indicated above is preferred for industrial practice.

As the result of continuous investigations to solving the aforesaid theme, the inventors have further found that the compound of formula A ($R^1$=Aa) can be converted into the compound of formula A ($R^1$=Ab) by adding the mycelium of the D-aminoacid oxidizing enzyme producing strain belonging to the genus Trigonopsis or the treated mycelium to the compound of formula A ($R^1$=Aa) or the salt thereof, or further the fermented broth containing them and that the compound of formula A ($R^1$=Ab) can be easily dissolved in organic solvent, which simplifies greatly the separation and purification step thereof.

The compounds of formula A ($R^1$=Ab) thus produced shows excellent antimicrobial activities and also are more useful as the intermediates for producing 7-methoxycephalosporin derivatives having introduced to the 7-position other acyl groups since the compounds are soluble in organic solvents.

In this embodiment of this invention the D-aminoacid oxidizing enzyme producing strain belonging to the genus Trigonopsis are properly used. Such a strain can be selected from the type culture preserved in strain preservation institutions or can be isolated from soil. Also, for increasing the formation activity of the aimed material of formula A ($R^1$=Ab), mutants produced from the aforesaid strains by ordinary means can be profitably used in this invention. As the microorganism having the aforesaid D-aminoacid oxidizing enzyme activity, there is illustrated *Trigonopsis variabilis*. This strain is available from the Institute for Fermentation, Osaka, Japan under the strain number IFO 0755 (ATCC 10679) and strain number IFO 0671.

For producing the aimed material A ($R^1$=Ab) using the microorganism having such a D-aminoacid oxidizing enzyme activity, it is usually preferred that the microorganism is first cultivated and the mycelium or the treated mycelium thus obtained is added to the cephalosporin compound of general formula A ($R^1$=Aa) under proper condition. As the cultivation method of producing mycelium, it is usually preferred to employ an aerobic cultivation and it is more preferred to employ a liquid cultivation with stirring under aeration. Conventional culture media are usually used in this process.

That is, synthetic culture media, semi-synthetic culture media, or natural culture media can be used and as the composition for the culture media, glucose, sucrose, mannitol, glycerol, dextrin, starch, vegetable oil can be used as the carbon sources and meat extract, pepton, gluten meal, cotton seed meal, soybean meal, peanut meal, fish meal, corn steep liquor, dry yeast, yeast extract, ammonium sulfate, ammonium nitrate, urea, and other organic and inorganic nitrogen compounds are used as the nitrogen sources.

Also, if necessary, a metal salt such as sulfates, nitrates, chlorides, carbonates, phosphates, etc., of Na, K, Mg, Ca, Zn, Fe, etc., may be added to the culture medium. Furthermore, if necessary, methionine, cysteine, cystine, methyl oleate, lard oil, silicone oil, surface active agent, etc., may be added to the culture medium as a formation promotor or a defoaming agent. Desirable result is obtained by maintaining the pH of the culture medium at about 4–10, preferably 5–6.

In particular, when the culture medium contains D- (or DL-) aminoacid such as, for example, D- (or DL-) methionine, D- (or DL-) alanine, D- (or DL-) valine, etc., an excellent D-aminoacid oxidizing enzyme activity is obtained. The cultivation temperature is usually 18°–37° C., preferably about 30° C. The cultivation period of time differs according to the cultivation conditions, in particular the cultivation apparatus, composition of cultivation medium, cultivation temperature, etc., but it is preferable to complete the cultivation when the D-aminoacid oxidizing enzyme activity becomes maximum. Usually, 2-10 days of cultivation is proper.

The mycelium thus obtained or the treated mycelium is used as the D-aminoacid oxidation reaction of the starting material of formula A ($R^1=As$). In this case, the treated mycelium means the mycelium which was converted into a useful form for producing the aimed material A ($R^1=Ab$) by increasing the D-aminoacid oxidizing enzyme activity by the application of a proper treatment thereto. For example, the D-aminoacid oxidizing enzyme activity utilized in this invention usually exists in mycelium and hence the treated mycelium means the cell-free extract obtained by applying a physical and/or chemical means to the mycelium collected from the cultivation product of the D-aminoacid oxidizing enzyme producing strain, washed, or partially or completely purified D-aminoacid oxidizing enzyme obtained from the cell-free extract by the application of a known enzyme separation and purification method, or further the activated mycelium obtained by combining the partially or wholly purified D-aminoacid oxidizing enzyme to a water-insoluble polymer or an inorganic carrier by a physical or chemical means to provide a solid D-aminoacid oxidizing enzyme activator or mycelium and then subjecting the activator or mycelium to an activation treatment.

In this invention, the preparation and the recycle of the aforesaid soluble enzyme is restricted in practical use but the use of the insoluble enzymes such as the activated mycelium is profitable for industrial applications as they can be readily recovered and reused.

The activation treatment of the mycelium described above can be performed by giving to the mycelium a certain mild damage to an extent not to the collapse thereof. As examples of such activation treatment, there are illustrated a method wherein the mycelium is frozen at temperatures below −10° C. at a pH of about 3–4 and then, defrosted, a method wherein the mycelium is treated in a bath by one or more organic solvents such as, acetone, n-butanol, 2-phenyl ethanol, diethyl ether, cyclohexane, benzene, toluene, etc., a method wherein the mycelium is treated by 0.1–10% surface active agent, for example, a cationic surface active agent such as cetyltrimethyl ammonium, cetylpyridinium cetyldimethylbenzyl ammonium halide, etc., an anionic surface active agent such as dodecyl sulfate, an alkali metal alkylarylsulfonate, sodium desoxycholate etc., and a nonionic surface active agent such as sorbitan monolaurate, Triton X-100 (trade name), etc., in an aqueous solution thereof, a method wherein the mycelium is treated by a diluted aqueous solution of potassium hydroxide or sodium hydroxide, or a method wherein the mycelium is suspended in a high osmotic pressure solution, for example, 2M cane sugar solution and then the solution is quickly diluted with water. These activation treatments are influenced by various elements such as temperature, processing period of time, pH value, the concentration of reagent, etc., and hence it is necessary to select the activation condition.

Also, when the action of catalase usually existing in a mycelium is not inhibited, the oxidative decarboxylation to the aimed material A ($R^1=Ab$) becomes imperfect to form together the 7-(5-carboxy-5-oxovaleramido)-7-methoxycephalosporin derivative represented by the general formula B

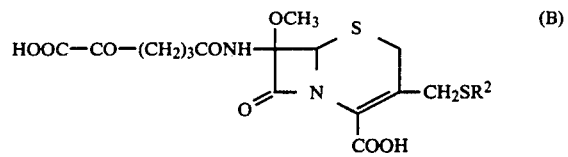

Therefore, in order to obtain selectively the aimed material A ($R^1=Ab$), it is desirable to inhibit the catalase activity. Examples of the proper catalase inhibitor are ascorbic acid, 3-amino-1,2,4-triazole, alkali metal azide, etc., and sodium azide is particularly preferable. The inhibitor may be added to the reaction mixture during the conversion of the starting material A ($R^1=Aa$) to the aimed material A ($R^1=Ab$) or the mycelium may be pretreated by the inhibitor before the mycelium is used in the aforesaid conversion. The amount of sodium azide used for the purpose is about 1–100 mM. Furthermore, the catalase in the aforesaid mycelium can be inactivated by subjecting the mycelium to a heat treatment before use in the aforesaid conversion step. That is, when the aforesaid mycelium is treated at 40°–60° C., preferably at 50° C. for at least 3 hours, it decreases remarkably the catalase activity but, the D-aminoacid oxidase activity remains as it is. The heat treatment may be simply performed to the mycelium in an aqueous solution or a buffer suspension but it is particularly effective to apply the mycelium for the simultaneous aforesaid heat treatment and "activation" reagent treatment. For example, by applying the activation treatment to the mycelium at 50° C. for 4 hours using a solvent, toluene, the inhibition of the catalase activity and the activation of the mycelium can be attained simultaneously.

The reaction of the enzyme system of the aforesaid activated mycelium and the starting material A ($R^1=Aa$) is usually performed at a pH of 6–8. It is desirable that the reaction be carried out at 30°–40° C. The reaction period of time is mainly depends upon the potency of the enzyme but is usually 1–5 hours.

Since the aforesaid enzyme reaction is performed under an aerobic condition, it is preferred to perform the reaction under aeration of air or oxygen.

As stated above, it is difficult to extract the starting material of formula A ($R^1=Aa$) from the fermented broth due to the amphoteric structure but according to the preferred embodiment of this invention, the recovery of the aimed product of formula A ($R^1=Ab$) can be practiced under a proper condition from the fermented broth of the starting material of formula A ($R^1=Aa$) after removing therefrom the mycelium, that is, the aimed material A ($R^1=Ab$) formed can be easily recovered by solvent extraction or the adsorption by ion-exchange resin. For example, the reaction product mixture is acidified to lower than pH 2.5 and then the aimed material is extracted from the reaction mixture with a suitable organic solvent such as ethyl acetate, n-butanol, etc. In this case, the use of the combination of an ion-exchange resin and a solvent extraction gives better results. Suitable ion-exchange resin is a liquid amine anionic exchange resin. Examples of the preferred solvents are ethyl acetate, butyl acetate, n-butanol, etc. Also, the aimed product can be separated using a solid ion-exchange resin. In this case, a proper solvent can be easily determined by a preliminary experiment.

For obtaining the pure product, conventional methods usually used for the purification of antibiotics can be used.

The aimed material of formula A ($R^1$=Ab) can be recovered not only in a free acid state but also in an ordinary alkali metal salt thereof, an alkaline earth metal salt, an organic amine salt, etc.

Several novel 7-methoxycephalosporin derivatives of formula A ($R^1$=Ab) of this invention are illustrated below together with the properties thereof.

V. 7-(4-Carboxybutyramido)-3-(5-carboxymethylthio-1,3,4-thiadiazol-2-yl)thiomethyl-7-methoxy-$\Delta^3$-cephem-4-carboxylic acid:

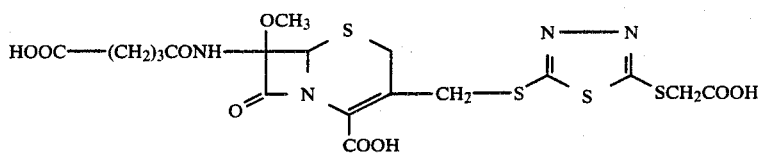

Starting material I: 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid;

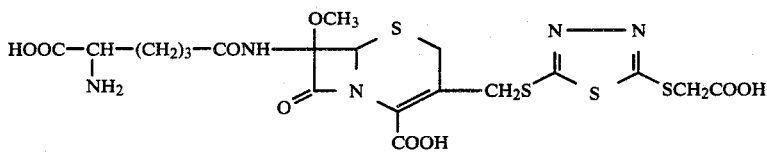

The physical and chemical properties of the aimed compound V of formula A ($R^1$=Ab,

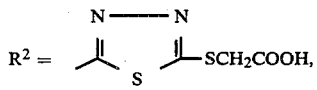

M=H) are as follows:

(1) White powder.
(2) Melting point 75°–78° C.
(3) Easily soluble in methanol and ethanol, soluble in water, ethyl acetate, butyl acetate, and butanol, but scarcely soluble in other organic solvents.
(4) Acidic material showing a ninhydrin reaction negative.
(5) Gives the ultraviolet absorption spectra as shown in FIG. 9 when measured in a 1/100M phosphate buffer solution having a pH of 6.5 and shows the absorption maximum at 278 m$\mu$.
(6) Gives the infrared absorption spectra as shown in FIG. 10 when measured as potassium bromide tablet and shows the absorption at 3250 cm$^{-1}$, 2925 cm$^{-1}$, 1770 cm$^{-1}$, 1715 cm$^{-1}$, 1520 cm$^{-1}$, 1380 cm$^{-1}$.
(7) The nuclear magnetic resonance spectra measured using TMS as the internal standard in heavy methanol is shown in FIG. 11, and shows the following signals:

$\delta$ value (ppm): 1.93 (2H, multiplet), 2.41 (4H, multiplet), 3.51 (3H, singlet), 3.37–3.81 (2H, quartet, J=18 Hz), 4.11 (2H, singlet), 4.15–4.63 (2H, quartet, J=14 Hz), 5.05 (1H, singlet).

(8) Gives the following elemental-analytical value for $C_{18}H_{20}N_4O_9S_4 \cdot 2H_2O$

|  | C | H | N |
|---|---|---|---|
| Calculated: | 35.99% | 4.03% | 9.33% |
| Found: | 35.77% | 3.81% | 9.42% |

(9) The mass spectra of the aimed material V measured after hydrolyzing the material in 6N hydrochloric acid for 2,5 hours at 100° C., extracting the hydrolyzed product with ethyl ether, drying the product by evaporation, and then silylating it with BSA (bistrimethyl silyl acetamide) give the fragment of m/e 276 $(CH_3)_3Si$—OOC—$CH_2$—$CH_2$—$CH_2$—COO—$Si(OH_3)_3$.

Considering from the above whole results, it is clear that the aimed compound is a 7-methoxycephalosporin compound from the presences of, in particular, the absorption at 1770 cm$^{-1}$ (cyclic lactem) in the infrared absorption spectra, and the signals of 3.51 p p m (3H, singlet, 7-OCH$_3$), 5.05 p p m (1H, singlet, 6-CH), 3.37–3.81 p p m (2H, quartet, J=18 Hz, 2-CH$_2$), 4.15–4.6 p p m (2H, quartet, J=14 Hz, 3-sidechain or CH$_2$), and further 4.11 p p m (2H, singlet, CH$_2$ of —S—CH$_2$—COOH) and further, from the facts that there are 1.93 p p m (2H, multiplet, $\beta$-CH$_2$) and 2.41 p p m (4H, multiplet, $\alpha,\gamma$-CH$_2$) showing the existence of 4-carboxybutyramido in the nuclear magentic resonance spectra and the mass spectra of the derivative of the aimed material which was hydrolyzed by hydrochloric acid and silylated gives the fragment of m/e 276, the aimed compound V of this invention has been determined to have the aforesaid structure that the 5-amino-5-carboxyvaleramido group at the 7-position of the starting material has been oxidatively deaminated to 4-carboxybutyramido group.

VI. 7-(4-Carboxybutyramido)-7-methoxy-3-(1-methyl-1H-tetrazol-5-yl)thiomethyl-$\Delta^3$-cephem-4-carboxylic acid:

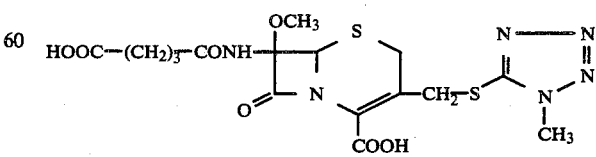

Starting material II: 7-(5-amino-5-carboxyvaleramido)-7-methoxy-3-(1-methyl-1H-tetrazol-5-yl)thiomethyl-$\Delta^3$-cephem-4-carboxylic acid.

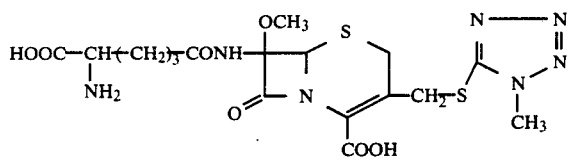

The physical and chemical properties of the aimed compound VI of formula A ($R^1$=Ab,

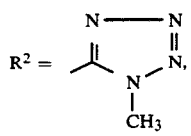

M=H) are as follows:

(1) White powder.

(2) Melting point 80°–83° C.

(3) Easily soluble in methanol and ethanol, soluble in water, ethyl acetate, butyl acetate, and butanol but scarcely soluble in other organic solvents. Sodium salt is easily soluble in water (4) Acidic material having ninhydrin reaction negative.

(5) Gives the ultraviolet absorption spectra as shown in FIG. 12 when measured in 1/100M phosphate buffer solution having a pH of 6.5 and has the absorption maximum at 269 mμ.

(6) Gives the infrared absorption spectra as shown in FIG. 13 when measured as potassium bromide tablet and shows the absorptions at 3420 cm$^{-1}$, 2940 cm$^{-1}$, 1765 cm$^{-1}$, 1680 cm$^{-1}$, 1610 cm$^{-1}$, 1525 cm$^{-1}$, 1390 cm$^{-1}$.

(7) The nuclear magnetic resonance spectra measured using TMS as the internal standard in heavy methanol gives, as shown in FIG. 14, the following signals:

δvlaue (p p m): 1.94 (2H, multiplet), 2.40 (4H, multiplet), 3.51 (3H, singlet), 3.40–3.83 (2H, quartet, J=18 Hz), 3.99 (3H, singlet), 4.17–4.50 (2H, quartet, J=14 Hz), 5.02 (1H, singlet).

(8) Gives the following elemental-analytical value for $C_{16}H_{20}N_6O_7S_2 \cdot 2H_2O$

|  | C | H | N |
|---|---|---|---|
| Calculated: | 37.79% | 4.76% | 16.53% |
| Found: | 37.78% | 4.75% | 16.41% |

(9) The mass spectra of the aimed material VI measured after hydrolyzing the material in 6N hydrochloric acid for 2.5 hours at 100° C., extracting the hydrolyzed product with ethyl ether, drying it by evaporation, and silylating it by BSA (bistrimethylsilyl acetamide) gives the fragment of m/2 276 $(CH_3)_3Si$—OOC—$CH_2CH_2CH_2$—COOSi$(CH_3)_3$.

Considering from the above whole results, it is clear that the aimed compound is a 7-methoxycephalosporin compound in particular, the existence of the absorption at 1765 cm$^{-1}$ (cyclic lactam) in the infrared absorption spectra and the signals at 3.51 p p m (3H, singlet, 7-OCH$_3$), 5.02 p p m (1H, singlet, 6-CH), 3.99 p p m (3H, singlet, N—CH$_3$ of tetrazole), 3.40–3.83 p p m (2H, quartet, J=18 Hz, 2-CH$_2$), 4.17–4.50 p p m (2H, quartet, J=14 Hz, 3-side chain CH$_2$) and further from the facts that there are 1.94 p p m (2H, multiplet, β-CH$_2$) and 2.40 p p m (4H, multiplet, α,γ-CH$_2$) showing the existence of 4-carboxybutyramido in the nuclear magnetic resonance spectra and further the mass spectra of the derivative of the aimed material hydrolyzed with hydrochloric acid and silylated gives the fragment of m/e 276, the aimed compound VI of this invention has been decided to have the aforesaid structure that the 5-amino-5-carboxyvaleramido group at the 7-position of the starting material was oxidatively deaminated into a 4-carboxybutyramido group.

VII. 7-(4-Carboxybutyramido)-7-methoxy-3-(5-methyl-1,3,4-thiadiazol-2-yl)thiomethyl-Δ$^3$-cephem-4-carboxylic acid:

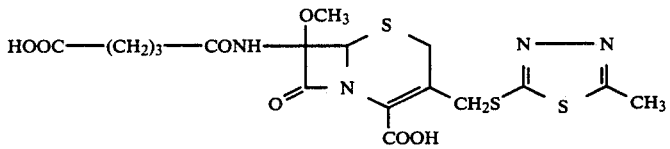

Starting material III:

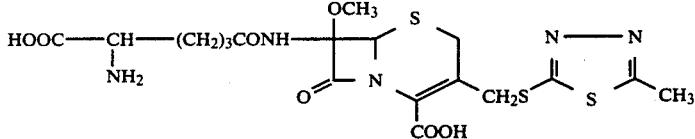

The physical and chemical properties of the aimed compound VII of this invention having formula A ($R^1$=Ab,

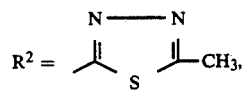

M=H) are as follows:

(1) White powder.

(2) Melting point 95°–99° C.

(3) Easily soluble in methanol and ethanol, soluble in water, ethyl acetate, butyl acetate, and butanol, but scarcely soluble in other organic solvents.

(4) Acidic material showing ninhydrin reaction negative.

(5) Gives the ultraviolet absorption spectra as shown in FIG. 15 when measured in a 1/100M phosphate buffer solution having a pH of 6.5 and has the absorption maximum at 273 mμ.

(6) Gives the infrared absorption spectra as shown in FIG. 16 when measured as potassium bromide tablet and shows the absorptions at 3260 cm$^{-1}$, 2925 cm$^{-1}$, 1773 cm$^{-1}$, 1515 cm$^{-1}$, and 1375 cm$^{-1}$.

(7) The nuclear magnetic resonance spectra measured using TMS as the internal standard in heavy methanol gives, as shown in FIG. 17, the following signals;

δ value (p p m): 1.92 (2H, multiplet), 2.40 (4H, multiplet), 2.71 (3H, singlet), 3.38–3.80 (2H, quartet, J=18 Hz), 3.51 (3H, singlet), 4.17–4.64 (2H, quartet, J=14 Hz), 5.03 (1H, singlet).

(8) Shows the following elemental-analytical value for $C_{17}H_{20}N_4O_7S_3$

|  | C | H | N |
|---|---|---|---|
| Calculated: | 41.79% | 4.13% | 11.47% |
| Found: | 41.89% | 4.27% | 11.17% |

(9) The mass spectra of the aimed material VII measured after hydrolyzing the material in 6N hydrochloric acid for 2.5 hours at 100° C., extracting the product with ethyl ether, drying the extract by evaporation, and silylating it with BSA (bistrimethylsilylacetamide) gives the fragment of m/e 276 $(CH_3)_3Si—OOC—CH_2CH_2CH_2—CO—OSi(CH_3)_3$.

Considering the above whole results, it is clear that the aimed compound is a 7-methoxycephalosporin compound from, in particular, the existences of the absorption at 1773 cm$^{-1}$ (cyclic lactam) in the infrared absorption spectra, and the signals at 3.51 p p m (3H, singlet, 7-OCH$_3$), 5.03 p p m (1H, singlet, 6-CH), 2.71 p p m (3H, singlet, C—CH$_3$ of thiadiazole), 3.38–3.80 p p m (2H, quartet, J=18 Hz, 2-CH$_2$), and 4.17–4.64 p p m (2H, quartet, J=14 Hz, 3-side chain CH$_2$), and further from the facts that there are 1.92 p p m (2H, multiplet, β-CH$_2$) and 2.40 p p m (4H, multiplet, α,γ-CH$_2$) showing the existence of 4-carboxybutyramido in the nuclear magnetic resonance spectra and further the mass spectra of the derivative prepared by hydrolyzing the aimed compound with hydrochloric acid and silylating the product gives the fragment of m/e 276, the aimed compound of formula VII has been decided to have the aforesaid structure that the 5-amino-5-carboxyvaleramido group at the 7-position of the starting material was oxidatively deaminated into the 4-carboxybutyramido group.

VIII. 7-(4-Carboxybutyramido)-7-methoxy-3-(1,3,4-thiadiazol-2-yl)thiomethyl-Δ$^3$-cephem-4-carboxylic acid:

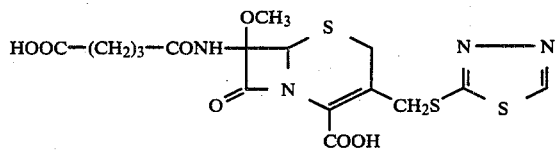

Starting material IV 7-(5-amino-5-carboxyvaleramido)-7-methoxy-3-(1,3,4-thiadiazol-2-yl)thiomethyl-Δ$^3$-cephem-4-carboxylic acid:

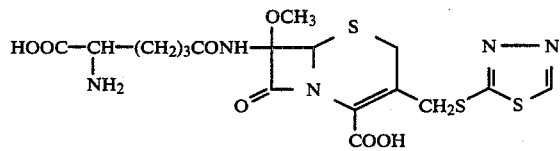

The physical and chemical properties of the aimed compound VII of formula A ($R^1$=Ab,

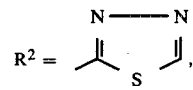

M=H are as follows:

(1) White powder.
(2) Melting point 88°–92° C.
(3) Easily soluble in methanol and ethanol, soluble in water, ethyl acetate, butyl acetate, and butanol, but scarcely soluble in other organic solvents.
(4) Acidic material showing a ninhydrin reaction negative.
(5) Gives the ultraviolet absorption spectra as shown in FIG. 18 when measured in a 1/100M phosphate buffer solution having a pH of 6.5 and has the absorption maximum at 274 mμ.
(6) Gives the infrared absorption spectra as shown in FIG. 19 when measured as potassium bromide tablet and shows the absorptions at 3250 cm$^{-1}$, 2925 cm$^{-1}$, 1770 cm$^{-1}$, 1515 cm$^{-1}$ and 1365 cm$^{-1}$.
(7) The nuclear magnetic resonance spectra measured using TMS as the internal standard in heavy methanol gives, as shown in FIG. 20, the following signals:

δ value (p p m): 1.92 (2H, multiplet), 2.40 (4H, multiplet), 3.39–3.83 (2H, quartet, J=18 Hz), 3.51 (3H, singlet), 4.24–4.73 (2H, quartet, J=14 Hz), 5.03 (1H, singlet), and 9.35 (1H, singlet).

(8) Shows the following elemental-analytical value for $C_{16}H_{18}N_4O_7S_3.\frac{1}{2}H_2O$

|  | C | H | N |
|---|---|---|---|
| Calculated: | 39.74% | 3.96% | 11.59% |
| Found: | 39.69% | 3.87% | 11.32% |

(9) The mass spectra of the aimed compound VIII measured after hydrolyzing the compound in 6N hydrochloric acid for 2.5 hours at 100° C., extracting the product with ethyl ether, drying the extract by evaporation, and silyating it with BAS (bistrimethylsilylacetamide) gives the fragment of m/e 276 $(CH_3)_3Si—OOC—CH_2CH_2CH_2—CO—OSi(CH_3)_3$.

Considering from the above whole results, it is clear that the aimed compound of this invention is a 7-methoxycephalosporin compound from the existences of the absorption at 1770 cm$^{-1}$ (cyclic lactam) in the infrared absorption spectra, and the signals at 3.51 p p m (3H, singlet, 7-OCH$_3$), 5.03 p p m (1H, singlet, 6-CH), 9.35 p p m (1H, singlet, CH of thiadiazole), 3.39–3.83 p p m (2H, quartet, J=18 Hz, 2-CH$_2$), and 4.24–4.73 ppm (2H, quartet, J=14 Hz, 3-side chain CH$_2$) and further from the facts that there are 1.92 p p m (2H, multiplet, —CH$_2$) and 2.40 p p m (4H, multiplet, α,γ-CH$_2$) showing the existence of 4-carboxybutyramido in the nuclear magnetic resonance spectra, and further the mass spectra of the derivative obtained by hydrolysing the aimed compound with hydrochloric acid and silylating the product gives the fragment of m/e 276, the the aimed compound VIII has been decided to have the aforesaid structure that the 5-amino-5-carboxyvaleramido group at the 7-position of the starting material was oxidatively deaminated into the 4-carboxybutyramido group.

Then, the results of analyzing the aimed compounds V–VII of this invention by thin layer chromatography and high speed liquid chromatography are shown in the following table together with the results about the starting materials I–IV of this invention also.

The Rf values by a thin layer chromatography using microcrystalline cellulose (Avicel, trade name) are as follows:

TABLE 1

|  | Solvent system | | Ninhydrin |
|---|---|---|---|
|  | 1 | 2 | coloring |
| Starting material I | 0.44 | 0.37 | + |
| Aimed compound V | 0.79 | 0.72 | − |
| Starting material II | 0.44 | 0.34 | + |
| Aimed compound VI | 0.81 | 0.64 | − |
| Starting material III | 0.42 | 0.44 | + |
| Aimed compound VII | 0.82 | 0.77 | − |
| Starting material IV | 0.42 | 0.36 | + |
| Aimed compound VIII | 0.81 | 0.65 | − |
| 7-(5-Amino-5-carboxy-valeramido)-3-[(3-p-hydroxyphenyl-2-methoxypropenoyl)oxymethyl]-7-methoxy-$\Delta^3$-cephem-4-carboxylic acid | 0.66 | 0.67 | + |
| 7-(4-Carboxybutyramido)-3-[(3-p-hydroxyphenyl-2-methoxypropenoyl)oxymethyl]-7-methoxy-$\Delta^3$-cephem-4-carboxylic acid | 0.67 | 0.67 | − |

Developing solvent system:
1. Isopropanol:n-butanol:acetic acid:water (21:3:7:9 by volume ratio)
2. n-Butanol:acetic acid:water (4:1:2 by volume ratio).

Detection: Ninhydrin reaction, or ultraviolet absorption (Manasulu Light, trade name, 2536 Å) or bioautography (*Proteus mirabilis* used).

The whole compounds showed positive in the latter two tests.

The results by a high speed liquid chromatography are shown in the following table.

TABLE 2

|  | Retention time |
|---|---|
| Starting material I | 3 min. 14 sec. |
| Aimed compound V | 13 min. 24 sec. |
| Starting material II | 1 min. 53 sec. |
| Aimed compound VI | 4 min. 54 sec. |
| Starting material III | 2 min. 55 sec. |
| Aimed compound VII | 11 min. 18 sec. |
| Starting material IV | 1 min. 56 sec. |
| Aimed compound VIII | 5 min. 28 sec. |

Solvent System: Acetonitrile: 0.1acetic acid (pH 3.3) (1:9 by volume ratio)

The retention times of the two cephalosporin compounds by a high speed liquid chromatography are as follows:

|  | Retention time |
|---|---|
| 7-(5-Amino-5-carboxy-valeramido)-3-[(3-p-hydroxyphenyl-2-methoxypropenoyl)oxymethyl]-7-methoxy-$\Delta^3$-cephem-4-carboxylic acid | 5 min. 18 sec. |
| 7-(4-Carboxybutyramido)-3-[(3-p-hydroxyphenyl-2-methoxypropenoyl)oxymethyl]-7-methoxy-$\Delta^3$-cephem-4-carboxylic acid. | 5 min. 55 sec. |

Used column: μ Bondapak C 18 (Water Ltd.)
Solvent system: Acetonitrile: 0.1% acetic acid (pH 3.3) (2:8 by volume ratio)

The in vivo effect of the compounds II, III, VI and VII are shown below:

Into 5 healthy male mice of ddY strain, $10^6$ cells of *E. coli* NIHJ were injected intraperitoneally, and after 2 hours each Sample was given subcutaneously, and survival % of after 5 days were shown in the following table. Similar experiments were carried out to $10^5$ cells of *Proteus mirabilis* 1287.

The control group each consists of 10 mice.

|  | *E coli* NIHJ | | | | *Proteus mirabilis* 1287 | | | |
|---|---|---|---|---|---|---|---|---|
|  | Doses (mg/mouse) | | | | | | | |
| Sample | 3 | 1 | 0.5 | 0 | 3 | 1 | 0.5 | 0 |
| II | 100 | 100 | 100 | 0 | 40 | 20 | 0 | 0 |
| III | 100 | 100 | 0 | 0 | 60 | 20 | 0 | 0 |
| VI | 80 | 80 | 40 | 0 | 100 | 20 | 20 | 0 |
| VII | 80 | 60 | 0 | 0 | 40 | 20 | 20 | 0 |

Then, the examples of this invention will be illustrated below in detail.

EXAMPLE 1

Preparation of 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid I:

A culture medium containing 1% starch, 1% glucose, 1.5% soybean flour 0.5% yeast extract, 0.1% dipotassium hydrogen phosphate, 0.05% magnesium sulfate, and 0.3% sodium chloride was placed in 500 ml. Sakaguchi flasks at 100 ml. each and sterilized at 120° C. for 20 minutes. Each medium was inoculated with *Streptomyces oganonensis* Y-G19Z strain and cultivated for 48 hours at 30° C.

The aforesaid another culture medium was placed in 2,000 ml. Sakaguchi flasks at 400 ml. each, sterilized at 120° C. for 20 minutes, and inoculated with the above inoculum at 2–3% concentration, followed by cultivation for 24 hours at 30° C. to provide a seed culture.

Furthermore, 60 liters of a culture medium containing 7% starch, 2% gluten meal, 2% soybean flour, 0.8% glycerol, 0.1% Casamino acid (acid hydrolyzed casein), 0.01% ferric sulfate, and 55 g. of sodium hydroxide was charged in each of two 100 liter fermentors together with 10 ml. of Adecanol (a non-ionic surface active agent) (trade name) as a defoaming agent and after sterilizing for 30 minutes at 120° C., each medium was inoculated with 800 ml. of the seed culture followed by cultivation for 24 hours at 30° C. In an aqueous sodium hydroxide solution, 5-mercapto-1,3,4-thiadiazole-2-thioacetic acid was dissolved and the solution thus formed was sterilized at high pressure and added to each fermentor up to 0.05% of the inoculum and cultivated for further 90 hours.

After the cultivation was completed, the cultured broth was adjusted to pH 2.0 and then mixed with Radiolite (trade name). The mixture was filtered using filter press and the filtrates were combined with each other to provide about 100 liters of a filtrate mixture.

The filtrate was adjusted to pH 3.0 with an aqueous sodium hydroxide solution, passed through a 12 liter Amberlite XAD-2 (trade name) column, and the column was washed with 30 liters of water, then eluted with 30 liters of an aqueous 50% acetone. The eluate thus collected was concentrated up to 5.5 liters and after removing impurities formed, water was added to the residue to make 10 liters of solution. The solution thus prepared was adjusted to pH 3.5 with a diluted aqueous hydrochloric acid solution and then passed through a 3 liter Amberlite IRA-68 (Cl-type) (trade name) column. After washing the column with 6 liters of water, elution was carried out using an aqueous solution (pH 7.2) containing 1M of sodium nitrate and 0.1M of sodium acetate to provide about 5 liters solution containing antimicrobially active material. The solution was adjusted to pH 3.0, passed through a one liter Amberlite XAD-2 (trade name) column, and after washing the column with water, the column was eluted with an aqueous solution of 50% acetone to provide about 400 ml. aqueous solution containing antimicrobially active material. By lyophilizing the solution, about 18 g. of the crude powder of the aimed compound I was obtained.

Then, 18 g. of the crude powder was subjected to a column chromatography using about 800 ml. of DEAE-Sephadex A-25 (acetic acid-type) (trade name) filled with a small amount of 0.5M ammonium bromide-acetic acid buffer solution and fractionated effective components. The antimicrobially active fractions obtained were collected, passed through a 500 ml. Amberlite XAD-2 (trade name) column, and after washing the column with water, the column was eluted with an aqueous solution of 25% acetone, and the eluate was evaporated to dryness.

Then, using a solvent mixture of isopropanol:water (7:3 by volume ratio), the product residue obtained was subjected to a column chromatogeaphy using microcrystalline cellulose (Avicel) prepared by a solvent mixture having the same composition as above. The antimicrobially active fraction obtained was spotted onto a thin layer plate of Avicel SF (trade name), developed by a mixture of isopropanol:n-butanol:acetic acid:-water (21:3:7:9 by volume ratio), and then a pyridine solution of 0.25% ninhydrin was sprayed onto it followed by heating to cause coloring. Then, the fractions showing a Rf value of 0.39 were collected. The fraction was vacuum evaporated to dryness at 45°–50° C. and then subjected to a column chromatography of microcrystalline cellulose (Avicel) prepared by a solvent mixture of isopropanol:n-butanol:acetic acid:water (21:3:7:9 by volume ratio). The antimicrobially active fraction thus obtained was then subjected to a thin layer chromatography of Avicel SF with the solvent mixture as above and by following the same procedure as above, the fractions showing 0.39 Rf value were collected and vacuum evaporated to dryness.

The product residue was further purified by a microcrystalline cellulose column chromatography using a solvent mixture of n-butanol:acetic acid:water (6:1.5:2.5 by volume ratio). The purified active fraction was evaporated to dryness and then dissolved in a small amount of distilled water. The solution was developed on a column of Sephadex G-10 (trade name) using distilled water. The fractions showing an antimicrobial activity were collected and subjected to a thin layer chromatography as stated above using a solvent mixture of n-butanol:acetic acid:water (6:1.5:2.5 by volume ratio). The fractions showing Rf 0.32 were collected, concentrated, and then subjected to lyophilization to provide about 80 mg. of white 7-(5-amino-5-carboxyvaleramido)-3-(5-carboxymethyl-1,3,4-thiadiazol-2-yl)thiomethyl-7-methoxy-$\Delta^3$-cephem-4-carboxylic acid.

EXAMPLE 2

Preparation of 7-(5-amino-5-carboxyvaleramido)-3-(1-methyl-1H-tetrazol-5-yl)thiomethyl-7-methoxy-$\Delta^3$-cephem-4-carboxylic acid II A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and sterilized for 20 minutes at 120° C. Then, each medium was inoculated with the *Streptomyces organonensis* Y-G19Z strain followed by cultivation for 48 hours at 30° C. Furthermore, the aforesaid culture medium was placed in two liter Sakaguchi flasks at 400 ml. each and after sterilizing for 20 minutes at 120° C., each medium was inoculated with up to 2–3% the cultivated broth prepared above followed by cultivation for further 24 hours at 30° C. to provide a inoculum.

Also, 60 liters of a culture medium containing 7% starch, 2% glutene meal, 2% soybean flour, 0.8% glycerol, 0.1% Casamino acid, 0.01% ferric sulfate, and 55 g. of sodium hydroxide was placed in two 100 liter fermentors each together with 10 ml. of Adecanol (trade name) as a defoaming agent and after sterilizing for 30 minutes at 120° C., each medium was inoculated with 800 ml. of the inoculum prepared above followed by cultivation for 24 hours at 30° C. Then, 1-methyl-5-mercapto-1H-tetrazole was dissolved in an aqueous sodium hydroxide solution and the solution was sterilized at high pressure and added to the cultivated broth to make the concentration thereof to 0.05%, and the mixture was further cultivated for 90 hours.

After the cultivation was completed, the cultivated broth thus formed was adjusted to pH 2.0 and then mixed with Radiolite diatomaceous earth (trade name) with stirring. The mixture was filtered using a filter press and the filtrates obtained were combined to provide about 100 liters of a filtrate mixture.

The filtrate was adjusted to pH 3.0 with an aqueous sodium hydroxide solution, passed through a 12 liter Amberlite XAD-2 (trade name) column, and after washing the column with 30 liters of water, and the column was eluted with 30 liters of an aqueous solution of 50% acetone. The eluate was concentrated up to 5.5 liters and the concentrate was adjusted to pH 3.5 with a diluted aqueous hydrochloric acid solution and passed through a three liter Amberlite IRA-68 (Cl-type) (trade name) column. The column was washed with 6 liters of water and fractionated with an aqueous solution (pH 7.2) containing 1M sodium nitrate and 0.1M of sodium acetate to provide about 5 liters of a solution containing the antimicrobially active material. The solution was adjusted to pH 3.0, passed through a one liter Amberlite XAD-2 (trade name) column, washed with water, and eluted with an aqueous solution of 50% acetone to provide about 400 ml. of aqueous solution containing the antimicrobially active material. By lyophilizing the solution, about 54 g. of the crude powder of the aimed compound II was obtained. The crude powder was subjected to a column chromatography with about 800 ml. of DEAE Sephadex A-25 (acetic acid-type) (trade name) filled with a small amount of 0.5M ammonium bromide.acetic acid buffer solution to fractionate active components. The antimicrobially active fractions were collected, passed through a 500 ml. Abmerlite XAD-2

(trade name) column, and the column was washed with water and eluted with an aqueous solution of 25% acetone. The antimicrobially active fractions were collected and then vacuum evaporated to dryness.

The residue formed was subjected to a column chromatography using microcrystalline cellulose (Avicel) (trade name) filled with a mixed solvent of isopropanol:water (7:3 by volume ratio) with the solvent mixture having the same composition as above. The antimicrobially active fraction obtained were collected, spotted onto a thin layer plate of Avicel SF (trade name), developed by a mixed solvent of n-butanol:acetic acid:water (6:1.5:2.5 by volume ratio, and a solution of 0.25% ninhydrin-pyridine was sprayed onto it followed by heating to cause coloring. Then, the fractions showing the Rf 0.31 were collected. The fractions were concentrated under reduced pressure and dried and then the residue formed was subjected to a column chromatography of microcrystalline cellulose (Avicel) prepared by a solvent mixture of isopropanol:n-butanol:acetic acid:water (21:3:7:9 by volume ratio). The antimicrobially active fractions obtained were subjected to a thin layer chromatography of Avicel SF (trade name) with the solution mixture having the same composition as above and then by following the same procedure as above, the fractions showing the Rf 0.39 were collected and vacuum evaporated to dryness.

The residue thus formed was further subjected to a microcrystal line cellulose column chromatography using a solvent mixture of n-butanol:acetic acid:water (6:1.5:2.5 by volume ratio) to purify the effective component. The active fraction thus purified was vacuum evaporated to dryness, dissolved in a small amount of distilled water, and developed on a column of Sephadex G 10 (trade name) using distilled water. The fractions having antimicrobial activity were collected and subjected to a thin layer chromatography using a solvent mixture of n-butanol:acetic acid:water (6:1.5:2.5 by volume ratio) as stated above. Then, the fractions having the Rf 0.31 were collected, concentrated, and then lyophilized to provide about 60 mg. of white 7-(5-amino-5-carboxyvaleramido)-3-(1-methyl-1H-tetrazol-5-yl)thiomethyl-7-methoxy-$\Delta^3$-cephem-4-carboxylic acid.

EXAMPLE 3

Preparation of 7-(5-amino-5-carboxyvaleramido)-7-methoxy-3-(5-methyl-1,3,4-thiadiazol-2-yl)thiomethyl-$\Delta^3$-cephem-4-carboxylic acid III A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and sterilized for 20 minutes at 120° C. Each medium was then inoculated by *Streptomyces oganonensis* Y-G19Z strain and cultivated for 48 hours at 30° C. Another culture medium as described above was placed in two liter Sakaguchi flasks at 400 ml. each and sterilized for 20 minutes at 120° C. Each medium was inoculated with the cultivated broth prepared above at 2-3% concentration and then cultivated for 24 hours at 30° C. to provide a seed culture.

Separately, 60 liters of the culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with 10 ml. of Adecanol (trade name) as a defoaming agent, sterilized for 30 minutes at 120° C., and inoculated by 800 ml. of seed culture followed by cultivation for 24 hours at 30° C. Then, 2-mercapto-5-methyl-1,3,4-thiadiazole was dissolved in aqueous sodium hydroxide solution, sterilized at high pressure, and added to the cultivated broth so that the concentration of it became 0.05% of the broth followed by further cultivation for 90 hours.

After the cultivation was completed, the cultivated broth was adjusted to pH 2.0 and mixed with Radiolite (trade name) with stirring. The mixture was filtered using filter press and the filtrates were combined to provide about 100 liters of a filtrate mixture.

The filtrate was adjusted to pH 3.0 by the addition of an aqueous sodium hydroxide solution, passed through a 12 liters Amberlite XAD-2 (trade name) column, and the column was washed with 30 liters of water, and eluted with 30 liters of aqueous solution of 50% acetone. The eluate was concentrated to 5.5 liters and the concentrate was adjusted to pH 3.5 with a diluted aqueous hydrochloric acid solution and passed through a 3 liters Amberlite IRA-68 (Cl-type) (trade name) column. The column was washed with 6 liters of water and eluted with an aqueous solution (pH 7.2) containing 1M sodium nitrate and 0.1M sodium acetate to provide a solution containing about 5 liters of an antimicrobially active material. The solution was adjusted to pH 3.0, passed through a one liter Amberlite XAD-2 (trade name) column, and after washing the column with water, and the column was eluted with an aqueous solution of 50% acetone to provide about 400 ml. of an aqueous solution containing the antimicrobially active material. The product was lyophilized.

Using a solvent mixture of n-butanol:acetic acid:water (4:1:2 by volume ratio), the residue formed was subjected to a column chromatography using microcrystalline cellulose (Avicel) (trade name) filled with the solvent mixture having the same composition as above. Then, the antimicrobially active fractions obtained were fractionated and spotted onto a thin layer plate of Avicel SF (trade name), developed by a solvent mixture of isopropanol:n-butanol:acetic acid:water (21:3:7:9 by volumn ratio), and a pyridine solution of 0.25% ninhydrin was sprayed onto it to cause coloring under heating. Thus, the fractions showing the Rf 0.43 were collected, vacuum evaporated to dryness at 45°-50° C., and then subjected to a column chromatography of microcrystalline cellulose (Avicel) prepared by a solvent mixture of acetonitrile:water (7:3 by volume ratio). The antimicrobially active fraction obtained was subjected to a thin layer chromatography of Avicel SF (trade name) as in the above procedure and then the fractions showing the Rf of 0.43 were collected and evaporated to dryness to give 0.78 g of crude powder.

The powder was dissolved in a small amount of distilled water and developed on a column of Sephadex G 10 (trade name) using distilled water. The antimicrobially active fractions were fractionated and subjected to thin layer chromatography using a solvent mixture of n-butanol:acetic acid:water (4:1:2 by volume ratio) as stated above and the fractions showing the Rf 0.43 were collected, concentrated and lyophilized to provide 82 mg. of white 7-(5-amino-5-carboxyvaleramido)-7-methoxy-3-(5-methyl-1,3,4-thiadiazol-2-yl)-thiomethyl-$\Delta^3$-cephem-4-carboxylic acid.

EXAMPLE 4

By following the same procedure as in Example 1 using, in this example, a solution of bis(5-carboxymethylthio-1,3,4-thiadiazol-2-yl)disufide prepared by dissolving the disulfide in water-containing methanol and sterilized by filtration using Millipore filter in place of the solution of 5-mercapto-1,3,4-thiadiazol-2-thioacetic acid prepared in water using an aqueous sodium hydroxide solution and sterilizing at high pressure, 23 g. of the crude powder of the aimed compound I was prepared and by purifying the product as in Example 1, about 45 mg. of 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid (Aimed compound I) was obtained.

EXAMPLE 5

By following the same procedure as in Example 2 using, in this example, a solution of bis(1-methyl-1H-tetrazol-5-yl)disulfide prepared by dissolving the disulfide in water containing methanol and sterilizing by filtration using Millipore filter in place of a solution of 1-methyl-5-mercapto-1H-tetrazole prepared by dissolving the tetrazole in water using an aqueous solution of sodium hydroxide and sterilizing at high pressure, about 26 g. of the crude powder and the aimed compound II was obtained and by purifying the product as in Example 2, about 37 mg. of 7-(5-amino-5-carboxyvaleramido)-3-(1-methyl-1H-tetrazol-5-yl)thiomethyl-7-methoxy-$\Delta^3$-cephem-4-carboxylic acid (aimed compound II) was obtained.

EXAMPLE 6

By following the same procedure as in Example 3 using, in this example, a solution of bis(5-methyl-1,3,4-thiadiazol-2-yl)disulfide prepared by dissolving the disulfide in water-containing methanol and sterilizing by filtration using Millipore filter in place of the solution of 2-mercapto-5-methyl-1,3,4-thadiazole prepared in water using an aqueous sodium hydroxide solution and sterilizing at high pressure, about 19 g. of the crude powder of the aimed compound III was obtained and by purifying the product as in Example 3, about 50 mg. of 7-(5-amino-5-carboxyvaleramido)-7-methoxy-3-(5-methyl-1,3,4-thiadiazol-2-yl)thiomethyl-$\Delta^3$-cephem-4-carboxylic acid (Aimed compound III) was obtained.

EXAMPLE 7

Preparation of
7-(5-amino-5-carboxyvaleramido)-7-methoxy-3-(1,3,4-thiadiazol-2-yl)thiomethyl-$\Delta^3$-cephem-4-carboxylic acid IV A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each, sterilized for 20 minutes at 120° C., and inoculated by the *Streptomyces oganonensis* Y-G19Z strain followed by cultivation for 48 hours at 30° C. Another aforesaid culture medium was also placed in two liters Sakaguchi flasks at 400 ml. each, sterilized for 20 minutes at 120° C., and then inoculated by 2-3% the cultured broth prepared in the above procedure followed by further cultivation for 24 hours at 30° C. to provide an seed culture.

Separately, 60 liters of a culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with 10 ml. of Adecanol (trade name) as a defoaming agent, strilized for 30 minutes at 120° C., and inoculated by 800 ml. of the seed culture followed by cultivation for 24 hours at 30° C. Then, a solution of 2-mercapto-1,3,4-thiadiazole prepared by dissolving the thiadiazole in water using an aqueous solution of sodium hydroxide and sterilizing at high pressure was added to the cultured broth so that the concentration of the thiadiazole became 0.05% and then the system was further cultivated for 90 hours.

After the cultivation was completed, the cultured broth was adjusted to pH 2.0 and mixed with Radiolite (trade name) with stirring. The mixture was filtered using a filter press and the filtrates were combined to provide about 100 liters of the filtrate mixture.

The filtrate was adjusted to pH 3.0, passed through a 12 liter Amberlite XAD-2 (trade name) column, and the column was washed with 30 liters of water, and eluted by 30 liters of an aqueous solution of 50% acetone. The eluate was concentrated up to 5.5 liters. The concentrate was adjusted to pH 3.5 and passed through a 3 liter Amberlite IRA-68 (Cl-type) (trade name) column. The column was washed with 6 liters of water and eluted with an aqueous solution (pH 7.2) containing 1M of sodium nitrate and 0.1M of sodium acetate to provide about 5 liters of a solution containing an antimicrobially active material. The solution was adjusted to pH 3.0, passed through a one liter Amberlite XAD-2 (trade name) column, washed with water, and eluted by an aqueous solution of 50% acetone to provide about 400 ml. of an aqueous solution containing the antimicrobially active material. The solution was lyophilized.

Using a solvent mixture of n-butanol:acetic acid:water (4:1:2 by volume ratio), the residue formed was subjected to a column chromatography using microcrystalline cellulose (Avicel, trade name) prepared with the solvent mixture having the same composition as above. The antimicrobially active fractions were fractionated spotted onto a thin layer plate of Avicel (trade name), developed using a solvent mixture of isopropanol:n-butanol:acetic acid:water (21:3:7:9 by volume ratio), and a pyridine solution of 0.25% ninhydrin was sprayed onto it to cause coloring under heating. Then, the fractions showing the Rf of 0.39 were collected and vacuum evaporated to dryness at 45°–50° C. The product residue was subjected to a column chromatography of microcrystalline cellulose (Avicel) prepared by a solvent mixture of acetonitrile:water (7:3 by volume ratio). The antimicrobically active fractions were also subjected to a thin layer chromatography of Avicel SF as in the above procedure and then the fractions showing the RF 0.39 were collected, vacuum evaporated to dryness provide 0.92 g. of a crude powder.

The crude powder was dissolved in a small amount of distilled water and subjected to a column chromatography using Amberlite CG-50 (H-type) with distilled water and the antimicrobially active fractions were collected, concentrated, and lyophilized. The residue was dissolved in a small amount of distilled water and developed on a column of Sephadex G 10 (trade name) using distilled water. The antimicrobial activity of each fraction was checked and the effective fractions were subjected to a thin layer chromatography using a solvent mixture of n-butanol:acetic acid:water (4:1:2 by volume ratio) as described above. Then, the fractions showing the Rf 0.38 were collected, concentrated, and lyophilized to provide 75 mg. of white 7-(5-amino-5-carboxyvaleramido)-7-methoxy-3-(1,3,4-thiadiazol-2-yl)thiomethyl-$\Delta^3$-cephem-4-carboxylic acid.

EXAMPLE 8

(a) A culture medium of pH 6.0 consisting of 20 g. of glucose, 4 g. of potassium dihydrogen phosphate, 1 g. of magnesium sulfate, 2 g. of ammonium sulfate, 0.5 g. of calcium chloride, 0.1 g. of boric acid, 0.04 g. of ammonium molybdate, 0.04 g. of manganese sulfate, 0.04 g. of zinc sulfate, 0.045 g. of copper sulfate, 0.025 g. of ferrous sulfate, 20 meg. of biotin, 2 mg. of thiamine hydrochloride, 1 g. of DL-methionine, and 1000 ml. of water was placed in 500 ml. Erlenmyer flasks at 100 ml. each and after sterilizing by conventional way, each medium was inoculated with *Trigonopsis variabilis* IFO 0755 strain followed by shaking cultivation for 72 hours at 30° C.

After the cultivation was completed, about 1000 ml. of the cultured broth was collected and by subjecting the broth to centrifugation at 2,000 rpm. for 30 minutes at 4° C., the mycelium was collected and suspended in 500 ml. of a 0.1M pyrophosphate buffer solution having pH 8.1 to provide a mycelium suspension. To the mycelium suspension was added 5 ml. of Triton X-100 (trade name) and the mixture was shaked for 20–40 minutes at 37° C. to activate the mycelium. By subjecting then the shaked mixture to a centrifugation at 2000 r.p.m. for 30 minutes at 4° C., the activated mycelium was collected, washed twice with a pyrophosphate buffer solution of pH 7–8, and resuspended in 100–200 ml. of a 0.1M pyrophosphate buffer solution of pH 8.1 to provide a suspension of activated mycelium.

(b) In 10 ml. of a 0.1M pyrophosphate buffer solution of pH 8.1 containing 0.026% sodium azide was dissolved 54.5 mg. of 7-(5-amino-5-carboxyvaleramido)-7-methoxy-3-(1-methyl-1H-tetrazol-5-yl)thiomethyl-$\Delta^3$-cephem-4-carboxylic acid and after adding thereto 0.5 ml. of the activated mycelium suspension and the mixture was stirred under aeration in a water bath at 33° C. The reaction system was checked every 30 minutes by means of a Hitachi High Speed liquid chromatographic apparatus (using $\mu$ Bondapak $C_{18}$ made by Waters Co., Solvent system: acetonitrile:0.1% acetic acid (1:9 volume ratio) to determine the completion of the reaction. That is, the retention time of the starting material, 7-(5-amino-5-carboxyvaleramido)-7-methoxy-3-(1-methyl-1H-tetrazol-5-yl)thiomethyl-$\Delta^3$-cephem-4-carboxylic acid shows 1 minute 53 seconds, while the retention time of 7-(4-carboxybutyramido)-7-methoxy-3-(1-methyl-1H-tetrazol-5-yl)-thiomethyl-$\Delta^3$-cephem-4-carboxylic acid thus converted by the D-aminoacid oxidation shows 4 minutes 54 seconds.

After the reaction was over, the mycelium was removed by centrifugation and the supernatant was separated and recovered, adjusted to pH 1.5–2.0 with a diluted aqueous hydrochloric acid solution, and then extracted 4 times each time with equal volume of ethyl acetate. The ethyl acetate extracts were recovered and re-extracted with phosphate buffer solution of pH 6.0. The phosphate buffer solution was then adjusted to pH 1.5–2.0 with a diluted hydrochloric acid solution and further extracted 4 times each with equal volume of ethyl acetate. The ethyl acetate extracts were combined, dehydrated with anhydrous sodium sulfate, and evaporated to dryness. The product was developed using a column filled with micro crystalline cellulose (Avicel, trade name) and a solvent mixture of n-butanol:acetic acid:water (4:1:2 by volume ratio) with the solvent mixture having the same composition as above and fractionated. The antimicrobial activity of each fraction to *Proteus mirabilis* was checked and the fractions having the antimicrobial activity were selected, spotted onto a thin layer plate of Avicel SF (trade name), and developed by a solvent mixture of isopropanol:n-butanol:acetic acid:water (21:3:7:9 by volume ratio) and a solvent mixture of n-butanol:acetic acid:water (4:1:2 by volume ratio). Then, the fractions showing the ultraviolet absorption to a Manasulu Light 2536 Å (made by Manasulu Kagaku Kogyo K. K.) and showing Rf 0.81 and Rf 0.64 respectively were collected, concentrated, and lyophilized to provide 35 mg. of pure 7-(4-carboxybutyramido)-7-methoxy-3-(1-methyl-1H-tetrazol-5-yl)thiomethyl-$\Delta^3$-cephem-4-carboxylic acid. This material showed antimicrobial activity to *Proteus mirabilis*, *Salmonella gallinarum*, and *Escherichia coli*.

EXAMPLE 9

In 10 ml. of a 0.1M pyrophosphate solution of pH 8.1 containing 0.026% sodium azide was dissolved 50 mg. of 7-(5-amino-5-carboxyvaleramido)-7-methoxy-3-(5-methyl-1,3,4-thiadiazol-2-yl)thiomethyl-$\Delta^3$-cephem-4-carboxylic acid and to the solution was added 0.5 ml. of the activated mycelium suspension of *Trigonopsis variabilis* IFO 0755 obtained by the same manner as in Example 8. The mixture was stirred under aeration in a water bath at 33° C. to perform the D-amino acid oxidation and the completion of the reaction was determined by the same high speed liquid chromatography as in Example 8. The retention time of the starting material, 7-(5-amino-5-carboxyvaleramido)-7-methoxy-3-(5-methyl-1,3,4-thiadiazol-2-yl)thiomethyl-$\Delta$-cephem-4-carboxylic acid was 2 minutes 55 seconds and the retention time of 7-(4-carboxybutyramido)-7-methoxy-3-(5-methyl-1,3,4-thadiazol-2-yl)-thiomethyl-$\Delta^3$-cephem-4-carboxylic acid formed by the D-amino acid oxidation was 11 minutes 18 seconds.

After the reaction was over, the mycelium was removed at 4° C. and the supernatant was recovered, adjusted to pH 1.5–2.0 with a diluted hydrochloric acid solution, and extracted four times each time with equal volume of ethyl acetate. The ethyl acetate extracts were combined and extracted with a phosphate buffer solution of pH 6. The phosphate solution was adjusted to pH 1.5–2.0 and extracted again four times each time with equal volume of ethyl acetate. The ethyl acetate extracts were collected, dehydrated with anhydrous sodium sulfate, and vacuum evaporated to dryness. Using a column filled with microcrystalline cellulose (Avicel, trade name) by a solvent mixture of n-butanol:acetic acid:water (4:1:2 by volume ratio), the residue product was developed using the solvent mixture having the same composition as above. The fractions showing an antimicrobial activity to *Proteus mirabilis* were selected, spotted onto a thin layer plate of Avicel SF, and developed with a solvent mixture of isopropanol:n-butanol:acetic acid:water (21:3:7:9 by volume ratio) and a solvent mixture of n-butanol:acetic acid:water (4:1:2 by volume ratio) respectively. Then, the fractions showing the ultraviolet absorption to Manasulu Light 2536 Å (made by Manasulu Kagaku Kogyo K.K.) and also showing Rf 0.82 and Rf 0.77 respectively were collected, concentrated, and lyophilized to provide 32 mg. of pure 7-(4-carboxybutyramido)-7-methoxy-3-(5- methyl-1,3,4-thiadiazol-2-yl)thiomethyl-Δ³-cephem-4-carboxylic acid. This material shows an antimicrobial activity to *Proteus mirabilis, Salmonella Gallinarum* and *Escherichia coli.*

EXAMPLE 10

In 10 ml. of a 0.1M pyrophosphate buffer solution of pH 8.1 containing 0.026% sodium azide was dissolved 50 mg. of 7-(5-amino-5-carboxyvaleramido)-3-(5-carboxymethylthio-1,3,4-thiadiazol-2-yl)-thiomethyl-7-methoxy-Δ³-cephem-4-carboxylic acid and after adding to the solution 0.5 ml. of the activated mycelium suspension prepared by the same manner as in Example 8a the mixture was stirred by aeration in a water bath at 33° C. to perform the D-amino acid oxidation. The completion of the reaction was checked every 30 minutes by means of the Hitachi High Speed Liquid Chromatographyic Apparatus as in Example 8, That is, the retention time of the starting material 7-(5-amino-5-carboxyvaleramido)-3-(5-carboxymethylthio-1,3,4-thiadiazol-2-yl)thiomethyl-7-methoxy-Δ³-cephem-4-carboxylic acid showed 3 minutes 14 seconds and the retention time of 7-(4-carboxybutyramido)-3-(5-carboxymethylthio-1,3,4-thiadiazol-2-yl)-thiomethyl-7-methoxy-Δ³-cephem-4-carboxylic acid formed by the action of D-amino acid oxidative enzyme showed 13 minutes 24 seconds.

After the reaction was over, the mycelium was removed by centrifugation at 4° C., the supernatent was recovered and then adjusted to pH 1.5–2.0 with a diluted aqueous hydrochloric acid solution followed by extraction four times each with equal volume of ethyl acetate. The ethyl acetate extracts thus recovered were combined and re-extracted with a phosphate buffer solution at pH 6.0. The phosphate buffer solution was adjusted to pH 1.5–2.0 with a diluted aqueous hydrochloric acid solution and extracted again four times each time with an equal volume of ethyl acetate.

The ethyl acetate extract was collected, dehydrated with anhydrous sodium sulfate, and vacuum evaporated to dryness.

The residue was developed by a solvent mixture of n-butanol:acetic acid:water (4:1:2 by volume ratio) using a column filled with microcrystalline cellulose (Avicel, trade name) by using the solvent mixture having the same composition as above. The antimicrobial activity of each fraction was checked and the fractions having an antimicrobial activity to *Proteus mirabilis* were selected, spotted onto a thin layer plate of Avicel SF, and developed with a solvent mixture of isopropanol:n-butanol:acetic acid:water (21:3:7:9 by volume ratio) and a solvent mixture of n-butanol:acetic acid:water (4:1:2 by volume ratio) respectively. Then, the fractions showing the ultraviolet absorption to the Manasulu Light 2536 Å (made by Manasulu Kagaku Kogyo K. K.) and showing Rf 0.79 and 0.72 respectively were collected, concentrated and lyophilized to give 30 mg. of pure 7-(4-carboxybutyramido)-3-(5-carboxymethylthio-1,3,4-thiadiazol-2-yl)thiomethyl-7-methoxy-Δ³-cephem-4-carboxylic acid. This material shows an antimicrobial activity to *Proteus mirabilis, Salmonella Gallinarum,* and *Escherichia coli.*

EXAMPLE 11

(a) A culture medium containing 1% starch, 1% glucose, 1.5% soybean flour, 0.5% yeast extract, 0.1% di potassium hydrogen phosphate, 0.05% magnesium sulfate, and 0.3% sodium chloride was placed in 500 ml Sakaguchi flasks at 100 ml. each and sterilized for 20 minutes at 120° C. Each medium was inoculated with *Streptomyces oganonensis* Y-G19Z strain followed by cultivation for 48 hours at 30° C. Another culture medium was placed in two liter Sakaguchi flasks at 400 ml. each, sterilized for 20 minutes at 120° C. and inoculated with 2–3% the cultured broth prepared above followed by cultivation for 24 hours at 30° C. to give seed culture.

Separately, 6 liters of a culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with each 10 ml. of Adecanol (trade name), sterilized for 30 minutes at 120° C., and inoculated with 800 ml. of the seed culture prepared in the above procedure followed by cultivation for 24 hours at 30° C. Then, a solution of 5-mercapto-1-methyl-1H-tetrazole prepared by an aqueous sodium hydroxide solution and sterilizing at high pressure was added to the cultured broth to that the concentration of the tetrazole became 0.05%. The cultivation was further carried out for 90 hours.

After the cultivation was completed, the cultured broth was adjusted to pH 2.0 and mixed with Radiolite (trade name) with stirring. The mixture was filtered with a filter press and the filtrates were combined to provide 100 liters of a filtrate mixture containing 100 meg./ml. of 7-(5-amino-5-carboxyvaleramido)-7-methoxy-3-(1-methyl-1H-tetrazol-5-yl)-thiomethyl-Δ³-cephem-4-carboxylic acid.

(b) The filtrate was adjusted to pH 3.0, passed through a 12 liter Amberlite XAD-2 (trade name) column, and the column was washed with 30 liters of water, and eluted with 30 liters of an aqueous 50 acetone. The eluate was concentrated up to 5.5 liters and the concentrate was adjusted to pH 7.5 using an aqueous sodium hydroxide solution. After removing the insolubles formed, 320 ml. of the activated mycelium suspension of the *Trigonopsis variabilis* IFO 0755 strain prepared in Example 8a was added to the solution. The mixture was stirred under aeration for 4 hours, adjusted to pH 1.5–2.0 with an aqueous hydrochloric acid solution, and extracted four times each time using equal volume of ethyl acetate. The ethyl acetate extracts were collected and 20 liters of the ethyl acetate extract thus obtained was then re-extracted with 2 liters of a phosphate buffer solution of pH 6.0. The phosphate solution was further adjusted to pH 1.5–2.0 with aqueous hydrochloric acid and extracted again four times each time with equal volume of ethyl acetate. The ethyl acetate filtrates were combined and 8 liters of the extract thus obtained was evaporated in vacuum to dryness to provide about 15 g. of a crude material. The material was subjected to column chromatography using cellulose powder by the same manner as in Example 8b to provide 6.1 g. of white 7-(4-carboxybutyramido)-7-methoxy-3-(1-methyl-1H-tetrazol-5-yl)thiomethyl-Δ³-cephem-4-carboxylic acid.

EXAMPLE 12

A culture medium comprising 50 g. of glucose, 10 g. of peptone, 1 g. of potassium dihydrogen phosphate, 0.5 g. of magnesium sulfate, 10 g. of malt extract, 1 g. of DL-methionine, and 1,000 ml. of water having pH 6.0 was inoculated with the *Trigonopsis variabilis* IFO 0755 strain followed by cultivation as in Example 8a and 1,000 ml. of the cultured broth thus formed was collected. By subjecting 1,000 ml. of the cultured broth to a centrifugation at 2,000 r.p.m. at 4° C., and mycelium formed was collected. The mycelium was suspended in 200 ml. of a 0.1M pyrophosphate buffer solution of pH 8.1 and the suspension of the mycelium was placed in 500 ml. Erlenmeyer flasks at 50 ml. each. Then, after adding to the suspension 5 ml. of toluene, the activation was performed for one hour at 37° C. Thereafter, the activated mycelium was collected by a centrifugation for 30 minutes at 2,000 r.p.m. and then centrifugally washed with 200 ml. of a 0.1M pyrophosphate buffer solution of pH 8.1. The activated mycelium was suspended again in 200 ml. of a 0.1M pyrophosphate buffer solution at pH 8.1 and the suspension was stirred in a water bath at 50° C. to inactivate the catalase activity. Then, 5 ml. of the activated mycelium suspension was added to a solution of 100 mg. of 7-(5-amino-5-carboxyvaleramido)-7-methoxy-3-(1-methyl-1H-tetrazol-5-yl)thiomethyl-$\Delta^3$-cephem-4-carboxylic acid in 20 ml. of a 0.1M pyrophosphate buffer solution of pH 8.1 and after stirring the mixture under aeration for 5 hours at 33° C., the mixture was treated as in Example 8b to provide 7-(4-carboxybutyramido)-7-methoxy-3-(1-methyl-1H-tetrazol-5-yl)thiomethyl-$\Delta^3$-cephem-4-carboxylic acid.

EXAMPLE 13

The mycelium obtained from the *Trigonopsis variabilis* by the same manner as in Example 8a was frozen at temperatures below −20° C. for more than one hour, then allowed to stand at room temperature to melt it, and suspended in 200 ml. of a 0.1M pyrophosphate solution of pH 8.1. Then, 5 ml. of the suspension was added to a solution of 100 mg. of 7-(5-amino-5-carboxyvaleramido)-7-methoxy-3-(1-methyl-1H-tetrazol-5-yl)thiomethyl-$\Delta^3$-cephem-4-carboxylic acid in 20 ml. of a 0.1M pyrophosphate buffer solution of pH 8.1 containing 0.026% sodium azide and after stirring the mixture under aeration for 5 hours at 33° C., the mixture was treated by the same manner as in Example 8b to provide 7-(4-carboxybutyramido)-7-methoxy-3-(1-methyl-1H-tetrazol-5-yl)thiomethyl-$\Delta^3$-cephem-4-carboxylic acid.

EXAMPLE 14

To a solution of 50 mg. of 7-(5-amino-5-carboxyvaleramido)-3-(3-p-hydroxyphenyl-2-methoxypropenoyl)oxymethyl-7-methoxy-$\Delta^3$-cephem-4-carboxylic acid in 10 ml. of a 0.1M pyrophosphate buffer solution of pH 8.1 containing 0.026% sodium azide was added 0.5 ml. of the activated mycelium suspension obtained from the *Trigonopsis variabilis* by the same procedure as in Example 8a and then the mixture was treated as in Example 8b to provide 7-(4-carboxybutyramido)-3-(3-p-hydroxyphenyl-2-methoxypropenoyl)oxymethyl-7-methoxy-$\Delta^3$-cephem-4-carboxylic acid.

The fractions obtained were subjected to a thin layer chromatography of Avicell (trade name) using a solvent mixture of isopropanol:n-butanol:acetic acid:water (21:3:7:9 by volume ratio) and a solvent mixture of n-butanol:acetic acid:water (4:1:2 by volume ratio) and thus the fractions showing Rf 0.67 and Rf 0.67 respectively were collected. The fraction showed the retention time of 5 minutes and 55 seconds in a high speed liquid chromatography (using $\mu$ Bondapak $C_{18}$ made by Waters Co., Ltd.) and a solution mixture of acetonitrile:0.1% aqueous acetic acid (2:8 by volume ratio). The product showed negative in ninhydrin reaction.

EXAMPLE 15

(a) Preparation of 7-(5-amino-5-carboxyvaleraimdo)-3-(1-methyl-1H-tetrazol-5-yl)thiomethyl-7-methoxy-$\Delta^3$-cephem-4-carboxylic acid A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and each medium was strilized for 20 minutes at 120° C. The sterile culture medium was inoculated with the *Sreptomyces oganonensis* Y-G19Z strain followed by cultivation for 48 hours at 30° C. Another culture medium prepared as above was placed in two liter Sakaguchi flasks at 400 ml. each and after sterilizing the medium for 20 minutes at 120° C., the culture medium was inoculted with the cultured broth formed in the above procedure at 2–3% in amount and cultivated for 24 hours at 30° C. to provide seed culture.

Separately, 60 liters of a culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with each 10 ml. of Adecanol (trade name) as a defoaming agent. Each culture medium was sterilized for 30 minutes at 120° C. and inoculated with 800 ml. of the seed culture prepared in the above procedure. Then, to each fermentator was added a solution of 1-methyl-5-mercapto-1H-tetrazole prepared by an aqueous solution of sodium hydroxide and sterilized at high pressure so that the content became 0.05% and then the cultured broth was further cultivated for 90 hours.

After the cultivation was completed, the cultured broth was adjusted to pH 2.0 and mixed with Radiolite (trade name) with stirring. The mixture was filtrated by filter press and the filtrates were combined to provide about 100 liters of a filtrate mixture.

The mixture was adjusted to pH 3.0 by the addition of an aqueous sodium hydroxide solution, passed through a 12 liter Amberlite XAD-2 (trade name) column, and the column was washed with 30 liters of water, eluted with 30 liters of aqueous 50% acetone. The eluate was concentrated up to 5.5 liters and the concentrate was adjusted to pH 3.5 with a diluted aqueous hydrochloric acid solution, passed through a 3 liter Amberlite IRA-68 (Cl-type) (trade name) column, and the column was washed with 6 liters of water, and eluted with an aqueous solution (pH 7.2) containing 1N sodium nitrate and 0.1M sodium acetate to provide about 5 liter of solution containing an antimicrobially active material. The solution was adjusted to pH 3.0, passed through a one liter Amberlite XAD-2 (trade name) column, and the column was washed with water, and eluted with an aqueous 50% acetone to provide about 400 ml. of an aqueous solution containing the antimicrobially active material, which was lyophilized to give about 54 g. of a crude powder. The crude powder was subjected to column chromatography with about 800 ml. of DEAE Sephadex A-25 (acetic acid-type) (trade name) filled with a small amount of 0.5M ammonium bromide.acetic acid buffer solution to fractionate effective fractions. The antimicrobially active fractions thus collected were passed through 500 ml. of Amberlite XAD-2 (trade name) column, and the column was washed with water, and eluted with an aqueous 25% acetone. The eluate was then evaporated in vacuo to dryness.

The dried product was subjected to a column chromatography with a solvent mixture of isopropanol:water (7:3 by volume ratio) using microcrystalline cellulose (Avicel, trade name) filled with the solvent mixture having the same composition as above. Then, the fraction showing antimicrobial activity was spotted onto a thin layer plate of Avicel SF (trade name), developed by a solvent mixture of n-butanol:acetic acid:water (6:1.5:2.5 by volume ratio), and a pyridine solution of 0.25% ninhydrin was sprayed onto it to cause coloring under heating. Thus, the fractions showing Rf 0.31 were collected, evaporated in vacuo to dryness at 45°–50° C., and subjected to a column chromatography of microcrystalline cellulose (Avicel, trade name) prepared with a solvent mixture of isopropanol:n-butanol:acetic acid:water (21:3:7:9 by volume ratio). The antimicrobially active fractions were then selected and subjected to a thin layer chromatography of Avicel SF (trade name) and by following the same procedure as above, the fractions showing Rf 0.39 were collected and evaporated in vacuo to dryness.

The dried product was further subjected to a microcrystalline cellulose column chromatography using a solvent mixture of n-butanol:acetic acid:water (6:1.5:2.5 by volume ratio) to perform the purification of the effective components. The purified active fractions were dried by concentration, dissolved in a small amount of distilled water, and developed on a column of Sephadex G 10 (trade name) using distilled water. The antimicrobial activity of each fraction was checked and the effective fractions were selected, subjected to a thin layer chromatography as stated above using a solvent mixture of n-butanol:acetic acid:water (6:1.5:2.5 by volume ratio), and the fractions showing Rf 0.31 were collected, concentrated and lyophilized to provide about 60 mg. of white 7-(5-amino-5-carboxyvaleramido)-3-(1-methyl-1H-tetrazol-5-yl)-thiomethyl-7-methoxy-$\Delta^3$-cephem-4-carboxylic acid.

(b) Preparation of 7-(4-carboxybutyramido)-7-methoxy-3-(1-methyl-1H-tetrazol-5-yl)thiomethyl-$\Delta^3$-cephem-4-carboxylic acid In 10 ml. of a 0.1M pyrophosphate buffer solution of pH 8.1 containing 0.02% of sodium azido was dissolved 54.5 mg. of 7-(5-amino-5-carboxyvaleramido)-7-methoxy-3-(1-methyl-1H-tetrazol-5-yl)thiomethyl-$\Delta^3$-cephem-4-carboxylic acid prepared in the step (a) and after adding to the solution 0.5 ml. of the activated mycelium suspension prepared by the same manner as in Example 8a, the mixture was stirred under aeration in a water bath at 33° C.

The completion of the reaction was confirmed by checking the reaction system every 30 minutes by means of a Hitachi high speed chromatography apparatus (using $\mu$ Bandapak $C_{18}$ made by Waters Ltd., solvent system: acetonitrile:0.1% acetic acid solution of 1:9 by volume ratio). That is, the retention time of the starting material, 7-(5-amino-5-carboxyvaleramido)-7-methoxy-3-(1-methyl-1H-tetrazol-5-yl)thiomethyl-$\Delta^3$-cephem-4-carboxylic acid was 1 minute 53 seconds and the retention time of 7-(4-carboxybutyramido)-7-methoxy-3-(1-methyl-1H-tetrazol-5-yl)thiomethyl-$\Delta^3$-cephem-4-carboxylic acid produced by D-amino acid oxidation was 4 minutes 54 seconds. After the reaction was over, the mycelium was removed by centrifugation at 4° C. The supernatant was recovered, adjusted to pH 1.5–2.0 with a diluted aqueous hydrochloric acid solution, and extracted four times each time with equal volume of ethyl acetate. The ethyl acetate extracts were combined and then re-extracted with a phosphate buffer solution of pH 6.0. The phosphate buffer solution was then adjusted to pH 1.5–2.0 with a diluted hydrochloric acid solution and extracted again four times each time with equal volume of ethyl acetate. The ethyl acetate extracts were combined, dehydrated with anhydrous sodium sulfate, and evaporated in vacuo to dryness. The dried product was developed with a solvent mixture of n-butanol:acetic acid:water (4:1:2 by volume ratio) using a column filled with microcrystalline cellulose (Avicel, trade name) using the solvent mixture having the same composition as above. The antimicrobial activity of each fraction against *Proteus mirabilis* was checked and the fractions having the antimicrobial activity were selected, spotted onto a thin layer plate of Avicel SF (trade name), and developed with a solvent mixture of isopropanol:n-butanol:acetic acid:water (21:3:7:9 by volume ratio) and a solvent mixture of n-butanol:acetic acid:water (4:1:2 by volume ratio) to collect the fractions showing the ultraviolet absorption to Manasulu Light 2536 Å (made by Manasulu Kagaku Kogyo K. K.) and showing Rf 0.81 and Rf 0.64, respectively. The fractions were combined then concentrated and lyophilized to provide 35 mg. of pure 7-(4-carboxybutyramido)-7-methoxy-3-(1-methyl-1H-tetrazol-5-yl)thiomethyl-$\Delta^3$-cephem-4-carboxylic acid. This material thus produced showed an antimicrobial activity to *Proteus mirabilis, Salmonella gallinarum,* and *Escherichia coli.*

In addition, the methyl ester compound derived from the product obtained in this example by the process shown in following Reference example A coincided completely in structure with the corresponding compound produced by the synthetic process of Reference example B shown below.

REFERENCE EXAMPLE A

In 10 ml. of chloroform was suspended 100 mg. of 7-(4-carboxybutyramido)-7-methoxy-3-(1-methyl-1H-tetrazol-5-yl)-thiomethyl-$\Delta^3$-cephem-4-carboxylic acid and after adding to the suspension 4 ml. of a 1% diazomethane ether solution, the mixture was stirred for 30 minutes at room temperature. The reaction mixture obtained was washed with diluted acetic acid and water, dried with anhydrous magnesium sulfate, and concentrated under reduced pressure. The residue obtained was subjected to a column chromatography using a silica gel column and eluted with a solvent mixture of benzene:ethyl acetate (1:3 by volume ratio). The aimed fractions were collected and concentrated under reduced pressure to provide 80 mg. of methyl 7-methoxy-7-(4-methoxycarbonylbutyramido)-3-(1-methyl-1H-tetrazol-5-yl)thiomethyl-$\Delta^3$-cephem-4-carboxylate.

Infrared absorption spectra: $\nu_{max}^{KBr}$ cm$^{-1}$: 1780 (lactam

1725 (ester, carbonyl).

Nuclear magnetic resonance spectra (CDCl$_3$): δ: 2.03 (2H, —CO—CH$_2$—C$\underset{\sim\sim}{\text{H}_2}$—CH$_2$—CO—), 2.39 (4H, —CO—CH₂—CH₂—CH₂—CO—), 3.51 (3H, 7-position, —OCH₃), 3.64 (3H, CH₃—O—CO—(CH₂)₃—), 3.87 3H,
3.92 3H,

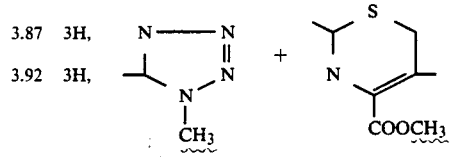

4.23, 4.53 (2H,

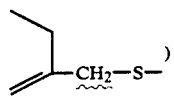

5.04 (1H, 6-position, —H).

REFERENCE EXAMPLE B (a) In a mixture of 30 ml. of ethyl acetate and 50 ml. of methanol were dissolved 1.0 g. of diphenylmethyl 7β-(3,5-di-tert-butyl-4-hydroxybenzylideneamino)-7α-methoxy-3-(1-methyl-1H-tetrazol-5-yl)thiomethyl-Δ³-cephem-4-carboxylate and 1.8 g. of a Gilard reagent and the mixture was stirred for 30 minutes at room temperature. After the reaction was over, the reaction mixture was concentrated under reduced pressure and the residue formed was dissolved in 50 ml. of ethyl acetate and washed three times each time with 20 ml. of water. The organic solvent layer formed was recovered, dried with anhydrous magnesium sulfate, and then the solvent was distilled away under reduced pressure to provide about 0.6 g. of crude diphenylmethyl 7β-amino-7α-methoxy-3-(1-methyl-1H-tetrazol-5-yl)thiomethyl-Δ³-cephem-4-carboxylate. The product was dissolved in 10 ml. of chloroform, and after cooling the solution to temperature of from −20° C. to −30° C., 0.6 g. of methyl 4-chloroformyl butyrate was added dropwise to the solution with stirring. The mixture was then further stirred for one hour at the same temperature. The reaction mixture was then mixed with 20 ml. of chloroform and the mixture was washed with 10 ml. of 1N hydrochloric acid and then 10 ml. of water. The organic solvent layer formed was recovered and dried with anhydrous magnesium sulfate. The solvent was distilled away under the reduced pressure and the residue formed was subjected to a silica gel chromatography. Then, the column was eluted with a solvent mixture of benzene:ethyl acetate (3:1 by volume ratio) and then a solvent mixture of benzene:ethyl acetate (1:3 by volume ratio) to provide 500 mg. of pure 7α-methoxy-7β-(4-methoxycarbonylbutyramido)-3-(1-methyl-1H-tetrazol-5-yl)thiomethyl-Δ³-cephem-4-carboxylate having the following properties.

Nuclear magnetic resonance spectra (CDCl₃): δ: 2.00 (2H, —CO—CH₂—CH₂—CH₂—CO—), 2.36 (4H, —CO—CH₂—CH₂—CH₂—CO—), 3,50 (3H, 7-position, —OCH₃), 3.63 (3H, CH₃—O—CO—(CH₂)₃—), 3.78 (3H,

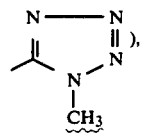

4.19, 4.44 (2H,

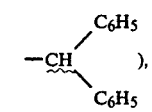

5.04 (1H, 6-position, H), 6.91 (1H,

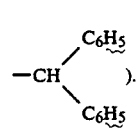

7.32 (10H,

—CH⟨C₆H₅ / C₆H₅⟩).

(b) In 4 ml. of a solvent mixture of trifluoroacetic acid:anisole (4:1 by volume ratio) was dissolved 400 mg. of diphenylmethyl 7α-methoxy-7β-(4-methoxycarbonylbutyramido)-3-(1-methyl-1H-tetrazol-5-yl)thiomethyl-Δ³-cephem-4-carboxylate at temperatures of from −10° C. to −20° C. and the mixture was stirred for 30 minutes at the same temperatures. After the reaction was over, the solvent was distilled away under reduced pressure and then ether was added to the residue, whereby crude 7α-methoxy-7β-(4-methoxycarbonylbutyramido)-3-(1-methyl-1H-tetrazol-5-yl)thiomethyl-Δ³-cephem-4-carboxylic acid precipitated, which was recovered by filtration and suspended in 10 ml. of chloroform. The suspension was mixed with 0.4 ml. of a 1% diazomethane ether solution at 10°-20° C. and the mixture was stirred for 30 minutes at room temperature. The reaction mixture formed was washed with a diluted acetic acid solution and then water and dried with anhydrous magnesium sulfate. Then, the solvent was distilled away under reduced pressure and the residue formed was subjected to a silica gel column chromatography. The column was eluted with a solvent mixture of benzene:ethyl acetate (1:3 by volume ratio) and the aimed fractions were collected and concentrated under reduced pressure to provide 150 mg. of methyl 7α-methoxy-7β-(4-methoxycarbonylbutyramido)-3-(1-methyl-1H-tetrazol-5-yl)thiomethyl-Δ³-cephem-4-carboxylate having the following properties:

Infrared absorption spectra: $\nu_{max}^{KBr}$ cm⁻¹: 1780 (lactam

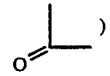

1725 (ester, carbonyl).

Nuclear magnetic resonance spectra (CDCl₃): δ: 2.03 (2H, —CO—CH₂—CH₂—CH₂—CO—), 2.39 (4H, —CO—CH₂—CH₂—CH₂—CO—), 3.51 (3H, 7-position —OCH₃), 3.64 (3H, $\underline{CH_3}$OCO(CH₂)₃—),

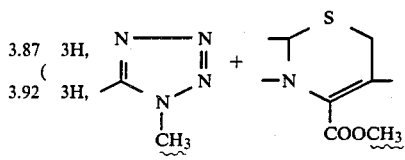

3.87 3H,
(
3.92 3H, 4.23, 4.53 (2H,

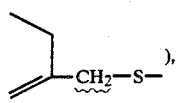

), 5.04 (1H, 6-position H).

EXAMPLE 16

(a) Preparation of 7-(5-amino-5-carboxyvaleramido)-7-methoxy-3-(5-methyl-1,3,4-thiadiazol-2-yl)thiomethyl-Δ³-cephem-4-carboxylic acid A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and each medium was sterilized for 20 minutes at 120° C. The culture medium was then inoculated with the *Streptomyces organonensis* Y-G19Z strain followed by cultivation for 48 hours at 30° C.

Another aforesaid culture medium was placed in 2 liter Sakaguchi flasks at 400 ml. each, sterilized for 20 minutes at 120° C., and then inoculated by 2-3% cultured broth prepared in the above procedure followed by cultivation for 24 hours at 30° C. to provide a seed culture.

Separately, 60 liters of a culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with 10 ml. of Adecanol (trade name), sterilized for 30 min. at 120° C., and then inoculated with 800 ml. of the seed culture prepared in the above procedure followed by cultivation for 24 hours at 30° C. To each fermentor was added a solution of 2-mercapto-5-methyl-1,3,4-thiadiazole prepared by aqueous sodium hydroxide solution and sterilizing at high pressure so that the content thereof became 0.05% of the culture broth and the cultivation was further carried out for 90 hours.

After the cultivation was completed, the cultured broth was adjusted to pH 2.0 and Radiolite (trade name) was added thereto with stirring. The mixture was filtrated using a filter press and the filtrates were combined to provide about 100 liters of a filtrate mixture.

The filtrate was adjusted to pH 3.0 by the addition of an aqueous sodium hydroxide solution, absorbed in a 12 liter Amberlite XAD-2 (trade name) column, and the column was washed with 30 liters of water, and eluted with 30 liters of an aqueous 50% acetone. The eluate was concentrated up to 5.5 liters, adjusted to pH 3.5 with a diluted aqueous hydrochloric acid solution, and absorbed in a 3 liter Amberlite IRA-68 (Cl-type) (trade name) column. The column was washed with 6 liters of water and eluted with an aqueous solution (pH 7.2) containing 1M of sodium nitrate and 0.1M of sodium acetate to provide about 5 liters of a solution containing an antimicrobially active material. The solution obtained was adjusted to pH 3.0, absorbed in one liter Amberlite XAD-2 (trade name) colume, and the column was washed with water, and eluted with an aqueous 50% acetone to provide about 400 ml. of an aqueous solution containing the antimicrobial material, which was lyophilized.

The product was subjected to a column chromatography with a solvent mixture of n-butanol:acetic acid:water (4:1:2 by volume ratio) using microcrystalline cellulose (Avicel, trade name) filled with the solvent mixture having the same composition as above and the antimicrobially active fractions obtained were spotted onto a thin layer plate of Avicel SF (trade name), developed by a solvent mixture of isopropanol:n-butanol:acetic acid:water (21:3:7:9 by volume ratio), and then a pyridine solution of 0.25% ninhydrin was sprayed to cause coloring under heating. Then, the fractions showing Rf 0.43 were collected evaporated to dryness under reduced pressure at 45°-50° C., and the product obtained was subjected to column chromatography of microstalline cellulose Avicel) prepared by a solvent mixture of acetonitrile:water (7:3 by volume ratio). The antimicrobially active fractions thus obtained were also subjected to thin layer chromatography of Avicel SF as in the above procedure and the fractions showing Rf 0.43 were collected and evaporated to dryness under reduced pressure to provide 0.78 g. of a crude powder.

The product was dissolved in a small amount of distilled water and developed on a column of Sephadex G 10 (trade name) using distilled water. The antimicrobial activity of each fraction was checked and the effective fractions were subjected to a thin layer chromatography as stated above using a solvent mixture of n-butanol:acetic acid:water (4:1:2 by volume ratio). Then, the fractions showing Rf 0.43 were collected, concentrated, and lyophilized to provide 82 mg. of white 7-(5-amino-5-carboxyvaleramido)-7-methoxy-3-(5-methyl-1,3,4-thiadiazol-2-yl)thiomethyl-Δ³-cephem-4-carboxylic acid.

(b) Preparation of 7-(4-carboxybutyramido)-7-methoxy-3-(5-methyl-1,3,4-thiadiazol-2-yl)thiomethyl-Δ³-cephem-4-carboxylic acid In 10 ml. of a 0.1M pyrophosphate buffer solution of pH 8.1 containing 0.026% sodium azide was dissolved 50 mg. of 7-(5-amino-5-carboxyvaleramido)-7-methoxy-3-(5-methyl-1,3,4-thiadiazol-2-yl)thiomethyl-Δ³-cephem-4-carboxylic acid and after adding to the solution 0.5 ml. of the activated mycelium suspension prepared using the *Trigonopsis variabilis* IFO 0755 strain as in Example 8a, the mixture was stirred under aeration in a water bath at 33° C. to perform the D-amino acid oxidation. The completion of the reaction was determined by the high speed liquid chromatography as in Example 8b. The retention time of the starting material, 7-(5-amino-5-carboxyvaleramido)-7-methoxy-3-(5-methyl-1,3,4-thiadiazol-2-yl)thiomethyl-66³-cephem-4-carboxylic acid was 2 minutes 55 seconds and that of 7-(4-carboxybutyramido)-7-methoxy-3-(5-methyl-1,3,4- thiadiazol-2-yl)thiomethyl-$\Delta^3$-cephem-4-carboxylic acid prepared by the D-amino acid oxidation was 11 minutes 18 seconds.

After the reaction was over, the mycelium was removed at 4° C. and the supernatant was recovered, adjusted to pH 1.5–2.0 with a diluted aqueous hydrochloric acid solution and extracted four times each time with equal volume of ethyl acetate. The ethyl acetate extracts were combined and re-extracted with a phosphate buffer solution of pH 6.0. The phosphate solution was then adjusted to pH 1.5–2.0 and then extracted again four times each time with equal volume of ethyl acetate. The ethyl acetate extracts were combined, dehydrated with anhydrous sodium sulfate, and evaporated to dryness. The product was developed with a solvent mixture of n-butanol:acetic acid:water (4:1:2 by volume ratio) using a column filled with microcrystalline cellulose (Avicel, trade name) by using the solvent mixture having the same composition as above. Then, the fractions showing the antimicrobial activity to *Proteus mirabilis* were selected, spotted onto a thin layer plate of Avicel SF (trade name) and developed with a solvent mixture of isopropanol:n-butanol:acetic acid:water (21:3:7:9 by volume ratio) and a solvent mixture of n-butanol:acetic acid:water (4:1:2 by volume ratio) to select the fractions showing the ultraviolet absorption to Manasulu light 2536 Å (made by Manasulu Kagaku Kogyo K. K.) and showing Rf 0.82 and Rf 0.77 respectively. The fractions thus collected were concentrated and then lyophilized to provide 32 mg. of pure 7-(4-carboxybutyramido)-7-methoxy-3-(5-methyl-1,3,4-thiadiazol-2-yl)thiomethyl-$\Delta^3$-cephem-4-carboxylic acid. This material showed an antimicrobial activity to *Proteus mirabilis, Salmonella gallinarum,* and *Escherichia coli.*

EXAMPLE 17

(a) Preparation of 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and sterilized for 20 minutes at 120°'C. Each culture medium was then inoculated with the *Streptomyces organonensis* Y-G19Z strain followed by cultivation for 48 hours at 30° C. Another aforesaid culture medium was placed in 2,000 ml Sakaguchi flasks at 400 ml. each and each culture medium was sterilized for 20 minutes at 120° C. and inoculated by 2–3% the cultured broth prepared in the above procedure followed by cultivation for 24 hours at 30° C. to provide seed culture.

Separately, 60 liters of a culture medium containing 7% starch, 2% gluten meal, 2% soybean flour, 0.8% glycerol, 0.1% Casamino acid, 0.01% ferric sulfate, and 55 g. of sodium hydroxide was placed in two 100 liter fermentors together with 10 ml. of Adecanol (trade name) as a defoaming agent. Racch medium was sterilized for 30 minutes at 120° C. and inoculated by 800 ml. of the seed culture prepared in the aforesaid procedure followed by cultivation for 24 hours at 30° C. Then, to each fermenter was added a solution of Bis(5-carboxymethylthio-1,3,4-thiadiazol-2-yl)disulfide prepared by dissolving the disulfide in water-containing methanol and sterilizing by filtration using a Millipore filter so that the content became 0.05% of the culture broth and then the cultivation was carried out for 90 hours.

After the cultivation was completed, the cultured broth was adjusted to pH 2.0 and mixed with Radiolite (trade name). The mixture was filtrated using a filter press and the filtrates were combined to provide about 100 liters of a filtrate mixture. The filtrate was adjusted to pH 3.0 by the addition of an aqueous sodium hydroxide solution, absorbed in a 12 liter Amberlite XAD-2 (trade name) column, and the column was washed with 30 liters of water, and eluted with 30 liters of an aqueous 50% acetone solution. The eluate was concentrated up to 5.5 liters and after removing insoluble matters formed, water was added to the concentrate to make 10 liters of the solution. The solution was adjusted to pH 3.5 with a diluted aqueous hydrochloric acid solution, passed through a 3 liter Amberlite IRA-68 (Cl-type) (trade name) column, and the column was washed with 6 liters of water, and eluted with an aqueous solution (pH 7.2) containing 1M of sodium nitrate and 0.1M of sodium acetate to provide about 5 liters of a solution containing an antimicrobially active material. The solution was adjusted to pH 3.0, absorbed in 1 liter Amberlite XAD-2 (trade name) column, and the column was washed with water, and eluted with an aqueous 50% acetone solution to provide about 400 ml. of an aqueous solution containing the antimicrobially active material. By lyophilizing the aqueous solution, about 23 g. of a crude powder was obtained.

Then, 2.3 g. of the crude powder was subjected to a column chromatography using about 800 ml. of DEAE-Sephadex A-25 (acetic acid-type) (trade name) filled with a small amount of 0.5M ammonium bromide acetic acid buffer solution to select the effective components. The antimicrobially active fractions were collected, absorbed in 500 ml. of Amberlite XAD-2 (trade name) column, and the column was washed with water, and eluted with an aqueous 25% acetone solution. The eluate was evaporated to dryness in vacuo.

The product was subjected to a column chromatography with a solvent mixture of isopropanol:water (7:3 by volume ratio) using microcrystalline cellulose (Avicel, trade name) filled using the solvent mixture having the same composition as above to fractionate antimicrobially active fractions. The fractions thus were spotted onto a thin layer plate of Avicel SF (trade name), developed with a solvent mixture of isopropanol:n-butanol:acetic acid:water (21:3:7:9 by volume ratio), and then a pyridine solution of 0.25% nihydrin was sprayed to cause coloring under heating. Then, the fractions showing Rf 0.39 were collected, evaporated to dryness under reduced pressure and then subjected to a column chromatography of microcrystalline cellulose (Avicel) prepared using a solvent mixture of isopropanol:n-butanol:acetic acid:water (21:3:7:9 by volume ratio). The antimicrobially active fractions were subjected to thin layer chromatography of Avicel SF with the solution mixture having the same composition as above and by following the same procedure as described above, the fractions showing Rf 0.39 were collected and evaporated in vacuo to dryness.

The concentrate was further purified by a microcrystalline cellulose column chromatography using a solvent mixture of n-butanol:acetic acid:water (6:1.5:2.5 by volume ratio). The purified active fractions were evaporated in vacuo to dryness, dissolved in a small amount of distilled water, and developed on a column of Sephadex G-10 (trade name) using distilled water. The antimicrobial activity of each fraction was checked and the effective fractions were subjected to a thin layer chromatography as stated above using a solvent mixture of n-butanol:acetic acid:water (6:1.5:2.5 by volume ratio). The fractions showing Rf 0.32 were collected, concentrated, and lyophilized to provide about 45 mg. of white 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid.

(b) Preparation of
7-(4-carboxybutyramido)-3-(5-carboxymethylthio-1,3,4-thiadiazol-2-yl)thiomethyl-7-methoxy-$\Delta^3$-cephem-4-carboxylic acid In 5 ml. of a 0.1M pyrophosphate buffer solution of pH 8.1 containing 0.026% sodium azide was dissolved 25 mg. of 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid prepared in above process (a) and after adding to the solution 0.5 ml. of the activated mycelium suspension prepared in Example 8a, the mixture was stirred under aeration in water at 33° C. to carry out the D-aminoacid oxidation. The completion of the reaction was checked every 30 minutes using the Hitachi high speed chromatography apparatus by the same manner as in Example 8a to determine the completion of the reaction. That is, the retention time of the starting material, 7-(5-amino-5-carboxyvaleramido)-3-(5-carboxymethylthio-1,3,4-thiadiazol-2-yl)thiomethyl-7-methoxy-$\Delta^3$-cephem-4-carboxylic acid was 3 minutes 14 seconds and that of 7-(4-carboxybutyramido)-3-(5-carboxymethylthio-1,3,4-thiadiazol-2-yl)thiomethyl-7-methoxy-$\Delta^3$-cephem-4-carboxylic acid prepared by the D-amino acid oxidation was 13 minutes 24 seconds.

After the reaction was over, the mycelium was removed by centrifugation at 4° C. and the supernatant was recovered, adjusted to pH 1.5–2.0 with a diluted aqueous hydrochloric acid solution and extracted four times each time with equal volume of ethyl acetate. The ethyl acetate extracts were conbined and re-extracted with a phosphate buffer solution of pH 6.0. The phosphate solution was adjusted to pH 1.5–2.0 with a diluted aqueous hydrochloric acid solution and extracted four times each time with equal volume of ethyl acetate. The ethyl acetate extracts were collected, dried over anhydrous sodium sulfate, and evaporated to dryness in vacuo.

The concentrate was developed with a solvent mixture of n-butanol:acetic acid:water (4:1:2 by volume ratio) using a column filled with microcrystalline cellulose (Avicel, trade name) using the aforesaid solvent mixture.

The antimicrobial activity of each fraction was checked and the fractions showing the antimicrobial activity to Proteus mirabilis were spotted onto a thin layer plate of Avicel SF, and developed by a solvent mixture of isopropanol:n-butanol:acetic acid:water (21:3:7:9 by volume ratio) and a solvent mixture of n-butanol:acetic acid:water (4:1:2 by volume ratio) respectively to collect the fractions showing the ultraviolet absorption to Manasulu light 2536 Å (made by Manasulu Kagaku Kogyo K. K.) and showing Rf 0.79 and Rf 0.72, respectively. The fractions were concentrated and lyophilized to provide 16 mg. of pure 7-(4-carboxybutyramdio)-3-(5-carboxymethylthio-1,3,4-thiadiazol-2-yl)thiomethyl-7-methoxy-$\Delta^3$-cephem-4-carboxylic acid. This material showed an antimicrobial activity to *Proteus mirabilis, Salmonella gallinarum,* and *Escherichia coli.*

EXAMPLE 18

In 10 ml. of a 0.1M pyrophosphate buffer solution of pH 8.1 containing 0.026% sodium azide was dissolved 50 mg. of 7-(5-amino-5-carboxyvaleramido)-7-methoxy-3-(1,3,4-diadiazol-2-yl)thiomethyl-$\Delta^3$-cephem-4-carboxylic acid and after adding thereto 0.5 ml. of the activated mycelium suspension prepared using the *Trigonopsis variabilis* as in Example 8a, and the mixture was stirred under aeration in a water bath of 33° C. to perform the D-amino acid oxidation. The completion of the reaction was determined by the same high speed liquid chromatography as in Example 8b. The retention time of the starting material, 7-(5-amino-5-carboxyvaleramido)-7-methoxy-3-(1,3,4-thiadiazol-2-yl)thiomethyl-$\Delta^3$-cephem-4-carboxylic acid was 1 minute and 56 seconds and that of 7-(4-carboxybutyramido)-7-methoxy-3-(1,3,4-thiadiazol-2-yl)-thiomethyl-$\Delta^3$-cephem-4-carboxylic acid formed by the D-amino acid oxidation was 5 minutes 28 seconds.

After the reaction was over, the mycelium was removed at 4° C. and the supernatant was recovered, adjusted to pH 1.5–2.0 with a diluted aqueous hydrochloric acid solution, and extracted four times each time with a equal volume of ethyl acetate. The ethyl acetate extracts were combined and re-extracted with a phosphate buffer solution of pH 6.0. The phosphate solution was extracted again four times each time with equal volume of ethyl acetate and the ethyl acetate extracts were collected, dried over anhydrous sodium sulfate, and evaporated to dryness in vacuo.

The product obtained was developed with a solvent mixture of n-butanol:acetic acid:water (4:1:2 by volume ratio) using a column filled with microcrystalline cellulose (Avicel, trade name) using the solvent mixture having the same composition as above to select the fractions showing the antimicrobial activity to *Proteus mirabilis.* The fractions thus selected were spotted onto a thin layer plate of Avicel SF and developed using a solvent mixture of isopropanol:n-butanol:acetic acid:water (21:3:7:2 by volume ratio) and a solvent mixture of n-butanol:acetic acid:water (4:1:2 by volume ratio) respectively to collect the fractions using the ultraviolet absorption to Manasulu Light 2536 Å (made by Manasulu Kagaku Kogyo K. K.) and showing Rf 0.81 and Rf 0.65, respectively. The fractions were concentrated and lyophilized to provide 40 mg. of pure 7-(4-carboxybutyramido)-7-methoxy-3-(1,3,4-thiadiazol-2-yl)thiomethyl-$\Delta^3$-cephem-4-carboxylic acid. This material showed an antimicrobial activity to *Proteus mirabilis, Salmonealla gellinarum,* and *Escherichia coli.*

EXAMPLE 19

(a) Preparation of
7-(5-amino-5-carboxyvaleramido)-7-methoxy-3-(1,3,4-thiadiazol-2-yl)thiomethyl-$\Delta^3$-cephem-4-carboxylic acid A culture medium containing 1% starch, 1% glucose, 1.5% soybean flour, 0.5% yeast extract, 0.1% dipotassium hydrogen phosphate, 0.05% magnesium sulfate, and 0.3% sodium chloride was placed in 500 ml. Sakaguchi flasks at 100 ml. each and sterilized for 20 minutes at 120° C. Then, each culture medium was inoculated with the *Streptomyces oganonensis* Y-G19Z followed by cultivation for 48 hours at 30° C.

Another aforesaid culture medium was placed in 2 liter Sakaguchi flasks at 400 ml. each and sterilized for 20 minutes at 120° C. Each culture medium was inoculated by the culture broth prepared in the above procedure and cultivated for 24 hours at 30° C. to provide a seed culture Separately, 60 liters of a culture medium containing 7% starch, 2% gluten meanl, 2% soybean flour, 0.8% glycerol, 0.1% Casamino acid, 0.01% ferric sulfate, and 55 g. of sodium hydroxide was placed in two 100 liter fermentors together with 10 ml. of Adecanol (trade name) as a defoaming agent and sterilized for 30 minutes at 120° C. Each culture medium was then inoculated by 800 ml. of the seed culture and cultivated for 24 hours at 30° C. Then, a solution of 2-mercapto-1,3,4-thiadiazole prepared by aqueous sodium hydroxide solution and sterilizing at high pressure was added to each fermenter so that the content became 0.05% of the culture broth and then the cultivation was further carried out for 90 hours.

After the cultivation was completed, the cultured broth was adjusted to pH 2.0 and mixed with Radiolite (trade name) with stirring. The mixture was filtered using a filter press and the filtrates were combined to provide about 100 liters of the filtrate mixture.

The filtrate was adjusted to pH 3.0 by adding an aqueous sodium hydroxide solution, charged into a 12 liter Amberlite XAD-2 (trade name) column, and the column was washed with 30 liters of water, and eluted with 30 liters of an aqueous 50% acetone solution. The eluate was concentrated up to 5.5 liters, adjusted to pH 3.5 with a diluted aqueous hydrochloride acid solution and charged into a 3 liter Amberlite IRA-68 (Cl-type) (trade name). The column was washed with 6 liters of water and eluted with an aqueous solution (pH 7.2) containing 1M of sodium nitrate and 0.1M sodium acetate to provide 5 liters of a solution containing an antimicrobially active material. The solution was adjusted to pH 3.0, charged into 1 liter of Amberlite XAD-2 (trade name) column, and the column was washed with water, and eluted with an aqueous 50% acetone solution to provide about 400 ml. of an aqueous solution containing the antimicrobially active material, which was lyophilized.

The product obtained was subjected to a column chromatography with a solvent mixture of n-butanol:acetic acid:water (4:1:2 by volume ratio) using microcrystalline cellulose (Avicel, trade name) filled in the column by using the solvent mixture having the same composition as above to select antimicrobially active fractions. The fractions were spotted onto a thin layer plate of Avicel SF (trade name), developed with a solvent mixture of isopropanol:n-butanol:acetic acid:water (21:3:7:9), and a pyridine solution of 0.25% ninhydrin was sprayed to cause coloring under heating. Then, the fractions showing Rf 0.39 was collected, evaporated to dryness under reduced pressure at 45°–50° C., and then subjected to a column chromatography of microcrystalline cellulose (Avicel) prepared by a solvent mixture of acetonitrile:water (7:3 by volume ratio). Then, the antimicrobially active fractions thus selected was subjected to a thin layer chromatography of Avicel SF by the manner as described above to collect the fractions showing Rf 0.39. The fractions were evaporated to dryness to provide 0.92 g. of a crude powder. The powder was dissolved in a small amount of distilled water and subjected to a column chromatography with distilled water using Amberlite CG-50 (H-type) to select antimicrobially active fractions. The fractions were then concentrated and lyophilized. The product was further dissolved in a small amount of distilled water and developed on a column of Sephadex G-10 (trade name) using distilled water. The antimicrobial activity of each fraction was checked and the effective fractions were subjected to a thin layer chromatography by the manner as stated above using a solvent mixture of n-butanol:acetic acid:water (4:1:2 by volume ratio) to collect the fractions showing Rf 0.38. The fractions were concentrated and lyophilized to provide 75 mg. of white 7-(5-amino-5-carboxyvaleramido)-7-methoxy-3-(1,3,4-thiadiazol-2-yl)-thiomethyl-$\Delta^3$-cephem-4-carboxylic acid.

(b) In 10 ml of a 0.1M phtophosphate buffer solution of pH 8.1 containing 0.026% sodium azide was dissolved 50 mg. of 7-(5-amino-5-carboxyvaleramido)-7-methoxy-3-(1,3,4-thiadiazol-2-yl)thiomethyl-$\Delta^3$-cephem-4-carboxylic acid and after adding to the solution 0.5 ml. of the activated mycelium suspension prepared using the *Trigonopsis variabilis* as in Example 8a, the mixture was stirred under aeration in a water bath at 33° C. to perform the D-amino acid oxidation. The completion of the reaction was determined by the same high speed liquid chromatography as in Example 8b. The retention time of the starting material, 7-(5-amino-5-carboxyvaleramido)-7-methoxy-3-(1,3,4-thiadiazol-2-yl)thiomethyl-$\Delta^3$-cephem-4-carboxylic acid was 1 minute 56 seconds and that of 7-(4-carboxybutyramido)-7-methoxy-3-(1,3,4-thiadiazol-2-yl)thiomethyl-$\Delta^3$-cephem-4-carboxylic acid formed by the D-amino acid oxidation was 5 minutes 28 seconds.

After the reaction was over, the mycelium was removed at 4° C. and the supernatant was recovered, adjusted to pH 1.5–2.0 with a diluted aqueous hydrochloric acid solution and extracted four times each time with equal volume of ethyl acetate. The ethyl acetate fractions were combined and re-extracted with phosphate buffer solution of pH 6.0. The phosphate solution was then adjusted to pH 1.5–2.0 and extracted again four times each time with equal volume of ethyl acetate. The ethyl acetate extracts were combined dehydrated over anhydrous sodium sulfate, and evaporated to dryness in vacuo. The product was developed with a solvent mixture of n-butanol:acetic acid:water (4:1:2 by volume ratio) using a column filled with microcrystalline cellulose (Avicel, trade name) by using the solvent mixture having the same composition as above to select the fractions showing an antimicrobial activity to *Proteus mirabilis*. The fractions were spotted ont a thin layer plate of Avicel SF and developed with a solvent mixture of isopropanol:n-butanol:acetic acid:water (21:3:7:9 by volume ratio) and a solvent mixture of n-butanol:acetic acid:water (4:1:2 by volume ratio) respectively to collect the fractions showing the ultraviolet absorption to Manasulu Light 2536 Å (made by Manasulu Kagaku Kogyo K. K.). The fractions were concentrated and lyophilized to provide 40 mg. of pure 7-(4-carboxybutyramido)-7-methoxy-3-(1,3,4-thiadiazol-2-yl)thiomethyl-$\Delta^3$-cephem-4-carboxylic acid. This material showed an antimicrobial activity against *Proteus mirabilis, Salmonella gallinarum,* and *Escherichia coli.*

EXAMPLE 20

Dry filled capsule containing 120 mg. of 7-(5-amino-5-carboxyvaleramido)-7-methoxy-3-(1-methyl-1H-tetrazol-5-yl)thiomethyl-$\Delta^3$-cephem-4-carboxylic acid.

|  | Per capsule |
|---|---|
| 7-(5-amino-5-carboxyvaleramido)-7-methoxy-3-(1-methyl-1H—tetrazol-5-yl)thiomethyl-$\Delta^3$-cephem-4-carboxylic acid | 120 mg. |
| Lactose | 20 mg. |
| Magnesium stearate | 5 mg. |
| Capsule No. 3 | 145 mg. |

The 7-(5-amino-5-carboxyvaleramido)-7-methoxy-3-(1-methyl-H-tetrazol-5-yl)thiomethyl-$\Delta^3$-cephem-4-carboxylic acid is reduced to a No. 60 powder and then lactose and magnesium stearate are passed through a No. 60 bolting cloth onto the powder and the combined ingredients admixed for ten minutes and then filled into No. 3 dry gelatin capsules.

EXAMPLE 21

Tablet containing 150 mg. of 7-(5-amino-5-carboxyvaleramido)-7-methoxy-3-(1-methyl-1H-tetrazol-5-yl)thiomethyl-$\Delta^3$-cephem-4-carboxylic acid.

| 7-(5-amino-5-carboxyvaleramido)-7-methoxy-3-(1-methyl-1H—tetrazol-5-yl)thiomethyl-$\Delta^3$-cephem-4-carboxylic acid | 150 mg. |
|---|---|
| Dicalcium phosphate J.P. (Japanese Pharmacopalia) | 115 mg. |
| Magnesium stearate | 3 mg. |
| Lactose J.P. | 39 mg. |

The active component is blended with the dicalcium phosphate and lactose. The mixture is granulated with 15% corn-starch paste (4 mg.) and rough-screened. It is dried at 40° C. and screened again through a No. 16 screen. The magnesium stearate is added and the mixture is compressed into tablets approximately 0.3 inch in diameter.

EXAMPLE 22

Parenteral solution containing 500 mg. of 7-(5-amino-5-carboxyvaleramido)-7-methoxy-3-(1-methyl-1H-tetrazol-5-yl)-thiomethyl-$\Delta^3$-cephem-4-carboxylic acid.

|  | Per ampoule |
|---|---|
| 7-(5-amino-5-carboxyvaleramido)-7-methoxy-3-(1-methyl-1H—tetrazol-5-yl)thiomethyl-$\Delta^3$-cephem-4-carboxylic acid | 500 mg |

The active compound (50.0 g.) is added in 150 ml of sterile water for injection and the obtained solution was adjusted to pH 8.0 by adding dilute sodium hydroxide and the volume of the solution was adjusted to 200 ml. The solution was divided into 100 ampoules, lyophilized and sealed.

We claim:
1. 7-(5-amino-5-carboxy-valeramido)-3-(1-methyl-1H-tetrazol-5-yl)thiomethyl-7-methoxy-$\Delta^3$-cephem-4-carboxylic acid.

* * * * *